US 7,579,510 B2

(12) United States Patent
Gadewar et al.

(10) Patent No.: US 7,579,510 B2
(45) Date of Patent: Aug. 25, 2009

(54) CONTINUOUS PROCESS FOR CONVERTING NATURAL GAS TO LIQUID HYDROCARBONS

(75) Inventors: Sagar B. Gadewar, Goleta, CA (US); Michael D. Wyrsta, Santa Barbara, CA (US); Philip Grosso, Auburn, CA (US); Aihua Zhang, Santa Barbara, CA (US); Eric W. McFarland, Santa Barbara, CA (US); Zachary J. A. Komon, Goleta, CA (US); Jeffrey H. Sherman, Sebastian, FL (US)

(73) Assignee: GRT, Inc., Santa Barbara, CA (US)

( * ) Notice: Subject to any disclaimer, the term of this patent is extended or adjusted under 35 U.S.C. 154(b) by 0 days.

(21) Appl. No.: 11/703,358

(22) Filed: Feb. 5, 2007

(65) Prior Publication Data
US 2007/0238909 A1 Oct. 11, 2007

Related U.S. Application Data

(60) Provisional application No. 60/765,115, filed on Feb. 3, 2006.

(51) Int. Cl.
C07C 2/88 (2006.01)
C07C 2/86 (2006.01)
(52) U.S. Cl. ..................... 585/310; 585/943
(58) Field of Classification Search ............ 585/310, 585/943
See application file for complete search history.

(56) References Cited

U.S. PATENT DOCUMENTS

| 2,168,260 | A | 8/1939 | Heisel et al. |
| 2,246,082 | A | 6/1941 | Vaughan et al. |
| 2,488,083 | A | 11/1949 | Gorin et al. |
| 2,677,598 | A | 5/1954 | Crummett et al. |
| 2,941,014 | A | 6/1960 | Rothweiler et al. |
| 3,172,915 | A | 3/1965 | Borkowski et al. |
| 3,246,043 | A | 4/1966 | Rosset et al. |
| 3,273,964 | A | 9/1966 | Rosset |
| 3,310,380 | A | 3/1967 | Lester |
| 3,346,340 | A | * | 10/1967 | Louvar et al. ............... 423/502 |

(Continued)

FOREIGN PATENT DOCUMENTS

BR 0210054 8/2004

(Continued)

OTHER PUBLICATIONS

U.S. Appl. No. 60/487,364, filed Jul. 15, 2003, inventor Lorkovic et al.

(Continued)

*Primary Examiner*—Thuan Dinh Dang
(74) *Attorney, Agent, or Firm*—Baker Botts L.L.P.

(57) ABSTRACT

An improved continuous process for converting methane, natural gas, or other hydrocarbon feedstocks into one or more higher hydrocarbons or olefins by continuously cycling through the steps of alkane halogenation, product formation (carbon-carbon coupling), product separation, and regeneration of halogen is provided. Preferably, the halogen is continually recovered by reacting hydrobromic acid with air or oxygen. The invention provides an efficient route to aromatic compounds, aliphatic compounds, mixtures of aliphatic and aromatic compounds, olefins, gasoline grade materials, and other useful products.

22 Claims, 8 Drawing Sheets

U.S. PATENT DOCUMENTS

| | | |
|---|---|---|
| 3,353,916 A | 11/1967 | Lester |
| 3,496,242 A | 2/1970 | Berkowitz et al. |
| 3,562,321 A | 2/1971 | Borkowski et al. |
| 3,598,876 A | 8/1971 | Bloch |
| 3,670,037 A | 6/1972 | Dugan |
| 3,673,264 A | 6/1972 | Kuhn |
| 3,679,758 A | 7/1972 | Schneider |
| 3,702,886 A | 11/1972 | Argauer et al. |
| 3,705,196 A | 12/1972 | Turner |
| 3,799,997 A | 3/1974 | Schmerling |
| 3,865,886 A | 2/1975 | Schindler et al. |
| 3,876,715 A | 4/1975 | McNulty et al. |
| 3,879,473 A | 4/1975 | Stapp |
| 3,879,480 A | 4/1975 | Riegel et al. |
| 3,883,651 A | 5/1975 | Woitun et al. |
| 3,886,287 A | 5/1975 | Kobayashi et al. |
| 3,894,103 A | 7/1975 | Chang et al. |
| 3,894,104 A | 7/1975 | Chang et al. |
| 3,894,105 A | 7/1975 | Chang et al. |
| 3,894,107 A | 7/1975 | Butter et al. |
| 3,907,917 A | 9/1975 | Forth |
| 3,919,336 A | 11/1975 | Kurtz |
| 3,920,764 A | 11/1975 | Riegel et al. |
| 3,923,913 A | 12/1975 | Antonini et al. |
| 3,928,483 A | 12/1975 | Chang et al. |
| 3,965,205 A | 6/1976 | Garwood et al. |
| 3,974,062 A | 8/1976 | Owen et al. |
| 3,987,119 A | 10/1976 | Kurtz et al. |
| 3,992,466 A | 11/1976 | Plank et al. |
| 4,006,169 A | 2/1977 | Anderson et al. |
| 4,011,278 A | 3/1977 | Plank et al. |
| 4,025,571 A | 5/1977 | Lago |
| 4,025,572 A | 5/1977 | Lago |
| 4,025,575 A | 5/1977 | Chang et al. |
| 4,025,576 A | 5/1977 | Chang et al. |
| 4,035,285 A | 7/1977 | Owen et al. |
| 4,035,430 A | 7/1977 | Dwyer et al. |
| 4,039,600 A | 8/1977 | Chang |
| 4,044,061 A | 8/1977 | Chang et al. |
| 4,046,825 A | 9/1977 | Owen et al. |
| 4,049,734 A | 9/1977 | Garwood et al. |
| 4,052,471 A | 10/1977 | Pearsall |
| 4,052,472 A | 10/1977 | Given et al. |
| 4,058,576 A | 11/1977 | Chang et al. |
| 4,060,568 A | 11/1977 | Rodewald |
| 4,071,753 A | 1/1978 | Fulenwider et al. |
| 4,072,733 A | 2/1978 | Hargis et al. |
| 4,087,475 A | 5/1978 | Jordan |
| 4,088,706 A | 5/1978 | Kaeding |
| 4,092,368 A | 5/1978 | Smith |
| 4,117,251 A | 9/1978 | Kaufhold et al. |
| 4,129,604 A | 12/1978 | Tsao |
| 4,133,838 A | 1/1979 | Pearson |
| 4,133,966 A | 1/1979 | Pretzer et al. |
| 4,138,440 A | 2/1979 | Chang et al. |
| 4,156,698 A | 5/1979 | Dwyer et al. |
| 4,169,862 A | 10/1979 | Eden |
| 4,172,099 A | 10/1979 | Severino |
| 4,187,255 A | 2/1980 | Dodd |
| 4,194,990 A | 3/1980 | Pieters et al. |
| 4,197,420 A | 4/1980 | Ferraris et al. |
| 4,219,680 A | 8/1980 | Konig et al. |
| 4,249,031 A | 2/1981 | Drent et al. |
| 4,270,929 A | 6/1981 | Dang Vu et al. |
| 4,272,338 A | 6/1981 | Lynch et al. |
| 4,282,159 A | 8/1981 | Davidson et al. |
| 4,300,005 A | 11/1981 | Li |
| 4,300,009 A | 11/1981 | Haag et al. |
| 4,301,253 A | 11/1981 | Warren |
| 4,302,619 A | 11/1981 | Gross et al. |
| 4,307,261 A | 12/1981 | Beard, Jr. et al. |
| 4,308,403 A | 12/1981 | Knifton |
| 4,311,865 A | 1/1982 | Chen et al. |
| 4,317,800 A | 3/1982 | Sloterdijk et al. |
| 4,317,934 A | 3/1982 | Seemuth |
| 4,317,943 A | 3/1982 | Knifton |
| 4,320,241 A | 3/1982 | Frankiewicz |
| 4,333,852 A | 6/1982 | Warren |
| 4,347,391 A | 8/1982 | Campbell |
| 4,350,511 A | 9/1982 | Holmes et al. |
| 4,371,716 A | 2/1983 | Paxson et al. |
| 4,373,109 A | 2/1983 | Olah |
| 4,376,019 A | 3/1983 | Gamlen et al. |
| 4,380,682 A | 4/1983 | Leitert et al. |
| 4,384,159 A | 5/1983 | Diesen |
| 4,410,714 A | 10/1983 | Apanel |
| 4,412,086 A | 10/1983 | Beard, Jr. et al. |
| 4,418,236 A | 11/1983 | Cornelius et al. |
| 4,431,856 A | 2/1984 | Daviduk et al. |
| 4,433,189 A | 2/1984 | Young |
| 4,433,192 A | 2/1984 | Olah |
| 4,439,409 A | 3/1984 | Puppe et al. |
| 4,440,871 A | 4/1984 | Lok et al. |
| 4,443,620 A | 4/1984 | Gelbein et al. |
| 4,462,814 A | 7/1984 | Holmes et al. |
| 4,465,884 A | 8/1984 | Degnan et al. |
| 4,465,893 A | 8/1984 | Olah |
| 4,467,130 A | 8/1984 | Olah |
| 4,467,133 A | 8/1984 | Chang et al. |
| 4,489,210 A | 12/1984 | Judat et al. |
| 4,489,211 A | 12/1984 | Ogura et al. |
| 4,492,657 A | 1/1985 | Heiss |
| 4,496,752 A | 1/1985 | Gelbein et al. |
| 4,497,967 A | 2/1985 | Wan |
| 4,499,314 A | 2/1985 | Seddon et al. |
| 4,506,105 A | 3/1985 | Kaufhold |
| 4,509,955 A | 4/1985 | Hayashi |
| 4,513,092 A | 4/1985 | Chu et al. |
| 4,513,164 A | 4/1985 | Olah |
| 4,523,040 A | 6/1985 | Olah |
| 4,524,227 A | 6/1985 | Fowles et al. |
| 4,524,228 A | 6/1985 | Fowles et al. |
| 4,524,231 A | 6/1985 | Fowles et al. |
| 4,538,014 A | 8/1985 | Miale et al. |
| 4,538,015 A | 8/1985 | Miale et al. |
| 4,540,826 A | 9/1985 | Banasiak et al. |
| 4,543,434 A | 9/1985 | Chang |
| 4,544,781 A | 10/1985 | Chao et al. |
| 4,547,612 A | 10/1985 | Tabak |
| 4,550,217 A | 10/1985 | Graziani et al. |
| 4,550,218 A | 10/1985 | Chu |
| 4,568,660 A | 2/1986 | Klosiewicz |
| 4,579,977 A | 4/1986 | Drake |
| 4,579,992 A | 4/1986 | Kaufhold et al. |
| 4,579,996 A | 4/1986 | Font Freide et al. |
| 4,587,375 A | 5/1986 | Debras et al. |
| 4,590,310 A | 5/1986 | Townsend et al. |
| 4,599,474 A | 7/1986 | Devries et al. |
| 4,605,796 A | 8/1986 | Isogai et al. |
| 4,605,803 A | 8/1986 | Chang et al. |
| 4,621,161 A | 11/1986 | Shihabi |
| 4,621,164 A | 11/1986 | Chang et al. |
| 4,633,027 A | 12/1986 | Owen et al. |
| 4,634,800 A | 1/1987 | Withers, Jr. et al. |
| 4,642,403 A | 2/1987 | Hyde et al. |
| 4,642,404 A | 2/1987 | Shihabi |
| 4,652,688 A | 3/1987 | Brophy et al. |
| 4,654,449 A | 3/1987 | Chang et al. |
| 4,655,893 A | 4/1987 | Beale |
| 4,658,073 A | 4/1987 | Tabak |
| 4,658,077 A | 4/1987 | Kolts et al. |
| 4,665,259 A | 5/1987 | Brazdil et al. |
| 4,665,267 A | 5/1987 | Barri |
| 4,665,270 A | 5/1987 | Brophy et al. |

| | | | | | |
|---|---|---|---|---|---|
| 4,675,410 A | 6/1987 | Feitler et al. | 5,055,634 A | 10/1991 | Volles |
| 4,690,903 A | 9/1987 | Chen et al. | 5,059,744 A | 10/1991 | Harandi et al. |
| 4,695,663 A | 9/1987 | Hall et al. | 5,068,478 A | 11/1991 | Miller et al. |
| 4,696,985 A | 9/1987 | Martin | 5,073,656 A | 12/1991 | Chafin et al. |
| 4,704,488 A | 11/1987 | Devries et al. | 5,073,657 A | 12/1991 | Warren |
| 4,704,493 A | 11/1987 | Devries et al. | 5,082,816 A | 1/1992 | Teller et al. |
| 4,709,108 A | 11/1987 | Devries et al. | 5,087,779 A | 2/1992 | Nubel et al. |
| 4,720,600 A | 1/1988 | Beech, Jr. et al. | 5,087,786 A | 2/1992 | Nubel et al. |
| 4,720,602 A | 1/1988 | Chu | 5,087,787 A | 2/1992 | Kimble et al. |
| 4,724,275 A | 2/1988 | Hinnenkamp et al. | 5,093,542 A | 3/1992 | Gaffney |
| 4,735,747 A | 4/1988 | Ollivier et al. | 5,097,083 A | 3/1992 | Stauffer |
| 4,737,594 A | 4/1988 | Olah | 5,099,084 A | 3/1992 | Stauffer |
| 4,748,013 A | 5/1988 | Saito et al. | 5,105,045 A | 4/1992 | Kimble et al. |
| 4,769,504 A | 9/1988 | Noceti et al. | 5,105,046 A | 4/1992 | Washecheck |
| 4,774,216 A | 9/1988 | Kolts et al. | 5,107,032 A | 4/1992 | Erb et al. |
| 4,775,462 A | 10/1988 | Imai et al. | 5,107,051 A | 4/1992 | Pannell |
| 4,777,321 A | 10/1988 | Harandi et al. | 5,107,061 A | 4/1992 | Ou et al. |
| 4,781,733 A | 11/1988 | Babcock et al. | 5,108,579 A | 4/1992 | Casci |
| 4,783,566 A | 11/1988 | Kocal et al. | 5,118,899 A | 6/1992 | Kimble et al. |
| 4,788,369 A | 11/1988 | Marsh et al. | 5,132,343 A | 7/1992 | Zwecker et al. |
| 4,788,377 A | 11/1988 | Chang et al. | 5,138,112 A | 8/1992 | Gosling et al. |
| 4,792,642 A | 12/1988 | Rule et al. | 5,139,991 A | 8/1992 | Taylor et al. |
| 4,795,732 A | 1/1989 | Barri | 5,146,027 A | 9/1992 | Gaffney |
| 4,795,737 A | 1/1989 | Rule et al. | 5,157,189 A | 10/1992 | Karra |
| 4,795,843 A | 1/1989 | Imai et al. | 5,160,502 A | 11/1992 | Kimble et al. |
| 4,795,848 A | 1/1989 | Teller et al. | 5,166,452 A | 11/1992 | Gradl et al. |
| 4,804,797 A | 2/1989 | Minet et al. | 5,175,382 A | 12/1992 | Hebgen et al. |
| 4,804,800 A | 2/1989 | Bortinger et al. | 5,178,748 A | 1/1993 | Casci et al. |
| 4,808,763 A | 2/1989 | Shum | 5,185,479 A | 2/1993 | Stauffer |
| 4,814,527 A | 3/1989 | Diesen | 5,188,725 A | 2/1993 | Harandi |
| 4,814,532 A | 3/1989 | Yoshida et al. | 5,191,142 A | 3/1993 | Marshall et al. |
| 4,814,535 A | 3/1989 | Yurchak | 5,194,244 A | 3/1993 | Brownscombe et al. |
| 4,814,536 A | 3/1989 | Yurchak | 5,202,506 A | 4/1993 | Kirchner et al. |
| 4,849,562 A | 7/1989 | Buhs et al. | 5,202,511 A | 4/1993 | Salinas, III et al. |
| 4,849,573 A | 7/1989 | Kaeding | 5,210,357 A | 5/1993 | Kolts et al. |
| 4,851,602 A | 7/1989 | Harandi et al. | 5,215,648 A | 6/1993 | Zones et al. |
| 4,851,606 A | 7/1989 | Ragonese et al. | 5,223,471 A | 6/1993 | Washecheck |
| 4,886,925 A | 12/1989 | Harandi | 5,233,113 A | 8/1993 | Periana et al. |
| 4,886,932 A | 12/1989 | Leyshon | 5,237,115 A | 8/1993 | Makovec et al. |
| 4,891,463 A | 1/1990 | Chu | 5,243,098 A | 9/1993 | Miller et al. |
| 4,895,995 A | 1/1990 | James, Jr. et al. | 5,243,114 A | 9/1993 | Johnson et al. |
| 4,899,000 A | 2/1990 | Stauffer | 5,245,109 A | 9/1993 | Kaminsky et al. |
| 4,899,001 A | 2/1990 | Kalnes et al. | 5,254,772 A | 10/1993 | Dukat et al. |
| 4,899,002 A | 2/1990 | Harandi et al. | 5,254,790 A | 10/1993 | Thomas et al. |
| 4,902,842 A | 2/1990 | Kalnes et al. | 5,264,635 A | 11/1993 | Le et al. |
| 4,925,995 A | 5/1990 | Robschlager | 5,268,518 A | 12/1993 | West et al. |
| 4,929,781 A | 5/1990 | James, Jr. et al. | 5,276,226 A | 1/1994 | Horvath et al. |
| 4,939,310 A | 7/1990 | Wade | 5,276,240 A | 1/1994 | Timmons et al. |
| 4,939,311 A | 7/1990 | Washecheck et al. | 5,276,242 A | 1/1994 | Wu |
| 4,945,175 A | 7/1990 | Hobbs et al. | 5,284,990 A | 2/1994 | Peterson et al. |
| 4,950,811 A | 8/1990 | Doussain et al. | 5,300,126 A | 4/1994 | Brown et al. |
| 4,950,822 A | 8/1990 | Dileo et al. | 5,306,855 A | 4/1994 | Periana et al. |
| 4,956,521 A | 9/1990 | Volles | 5,316,995 A | 5/1994 | Kaminsky et al. |
| 4,962,252 A | 10/1990 | Wade | 5,319,132 A | 6/1994 | Ozawa et al. |
| 4,973,776 A | 11/1990 | Allenger et al. | 5,334,777 A | 8/1994 | Miller et al. |
| 4,973,786 A | 11/1990 | Karra | 5,345,021 A | 9/1994 | Casci et al. |
| 4,982,024 A | 1/1991 | Lin et al. | 5,354,916 A | 10/1994 | Horvath et al. |
| 4,982,041 A | 1/1991 | Campbell | 5,354,931 A | 10/1994 | Jan et al. |
| 4,988,660 A | 1/1991 | Campbell | 5,366,949 A | 11/1994 | Schubert |
| 4,990,696 A | 2/1991 | Stauffer | 5,371,313 A | 12/1994 | Ostrowicki |
| 4,990,711 A | 2/1991 | Chen et al. | 5,382,704 A | 1/1995 | Krespan et al. |
| 5,001,293 A | 3/1991 | Nubel et al. | 5,382,743 A | 1/1995 | Beech, Jr. et al. |
| 5,004,847 A | 4/1991 | Beaver et al. | 5,382,744 A | 1/1995 | Abbott et al. |
| 5,013,424 A | 5/1991 | James, Jr. et al. | 5,385,718 A | 1/1995 | Casci et al. |
| 5,013,793 A | 5/1991 | Wang et al. | 5,395,981 A | 3/1995 | Marker |
| 5,019,652 A | 5/1991 | Taylor et al. | 5,399,258 A | 3/1995 | Fletcher et al. |
| 5,026,934 A | 6/1991 | Bains et al. | 5,401,890 A | 3/1995 | Parks |
| 5,026,937 A | 6/1991 | Bricker | 5,401,894 A | 3/1995 | Brasier et al. |
| 5,026,944 A | 6/1991 | Allenger et al. | 5,406,017 A | 4/1995 | Withers, Jr. |
| 5,034,566 A | 7/1991 | Ishino et al. | 5,414,173 A | 5/1995 | Garces et al. |
| 5,043,502 A | 8/1991 | Martindale et al. | 5,430,210 A | 7/1995 | Grasselli et al. |
| 5,055,235 A | 10/1991 | Brackenridge et al. | 5,430,214 A | 7/1995 | Smith et al. |
| 5,055,633 A | 10/1991 | Volles | 5,430,219 A | 7/1995 | Sanfilippo et al. |

| | | | | | | |
|---|---|---|---|---|---|---|
| 5,436,378 A | 7/1995 | Masini et al. | | 6,002,059 A | 12/1999 | Hellring et al. |
| 5,444,168 A | 8/1995 | Brown | | 6,015,867 A | 1/2000 | Fushimi et al. |
| 5,446,234 A | 8/1995 | Casci et al. | | 6,018,088 A | 1/2000 | Olah |
| 5,453,557 A | 9/1995 | Harley et al. | | 6,022,929 A | 2/2000 | Chen et al. |
| 5,456,822 A | 10/1995 | Marcilly et al. | | 6,034,288 A | 3/2000 | Scott et al. |
| 5,457,255 A | 10/1995 | Kumata et al. | | 6,072,091 A | 6/2000 | Cosyns et al. |
| 5,464,799 A | 11/1995 | Casci et al. | | 6,087,294 A | 7/2000 | Klabunde et al. |
| 5,465,699 A | 11/1995 | Voigt | | 6,090,312 A | 7/2000 | Ziaka et al. |
| 5,480,629 A | 1/1996 | Thompson et al. | | 6,096,932 A | 8/2000 | Subramanian |
| 5,486,627 A | 1/1996 | Quarderer, Jr. et al. | | 6,096,933 A | 8/2000 | Cheung et al. |
| 5,489,719 A | 2/1996 | Le et al. | | 6,103,215 A | 8/2000 | Zones et al. |
| 5,489,727 A | 2/1996 | Randolph et al. | | 6,107,561 A | 8/2000 | Thompson |
| 5,500,297 A | 3/1996 | Thompson et al. | | 6,117,371 A | 9/2000 | Mack |
| 5,510,525 A | 4/1996 | Sen et al. | | 6,124,514 A | 9/2000 | Emmrich et al. |
| 5,523,503 A | 6/1996 | Funk et al. | | 6,127,588 A | 10/2000 | Kimble et al. |
| 5,525,230 A | 6/1996 | Wrigley et al. | | 6,130,260 A | 10/2000 | Hall et al. |
| 5,563,313 A | 10/1996 | Chung et al. | | 6,143,939 A | 11/2000 | Farcasiu et al. |
| 5,565,092 A | 10/1996 | Pannell et al. | | 6,169,218 B1 | 1/2001 | Hearn et al. |
| 5,565,616 A | 10/1996 | Li et al. | | 6,180,841 B1 | 1/2001 | Fatutto et al. |
| 5,571,762 A | 11/1996 | Clerici et al. | | 6,187,871 B1 | 2/2001 | Thompson et al. |
| 5,571,885 A | 11/1996 | Chung et al. | | 6,187,983 B1 | 2/2001 | Sun |
| 5,600,043 A | 2/1997 | Johnston et al. | | 6,203,712 B1 | 3/2001 | Bronner et al. |
| 5,600,045 A | 2/1997 | Van Der Aalst et al. | | 6,207,864 B1 | 3/2001 | Henningsen et al. |
| 5,609,654 A | 3/1997 | Le et al. | | 6,225,517 B1 | 5/2001 | Nascimento et al. |
| 5,633,419 A | 5/1997 | Spencer et al. | | 6,248,218 B1 | 6/2001 | Linkous et al. |
| 5,639,930 A | 6/1997 | Penick | | 6,265,505 B1 | 7/2001 | McConville et al. |
| 5,653,956 A | 8/1997 | Zones | | 6,281,405 B1 | 8/2001 | Davis et al. |
| 5,656,149 A | 8/1997 | Zones et al. | | 6,337,063 B1 | 1/2002 | Rouleau et al. |
| 5,661,097 A | 8/1997 | Spencer et al. | | 6,342,200 B1 | 1/2002 | Rouleau et al. |
| 5,663,465 A | 9/1997 | Clegg et al. | | 6,369,283 B1 | 4/2002 | Guram et al. |
| 5,663,474 A | 9/1997 | Pham et al. | | 6,372,949 B1 | 4/2002 | Brown et al. |
| 5,675,046 A | 10/1997 | Ohno et al. | | 6,376,731 B1 | 4/2002 | Evans et al. |
| 5,675,052 A | 10/1997 | Menon et al. | | 6,380,328 B1 | 4/2002 | McConville et al. |
| 5,679,879 A | 10/1997 | Mercier et al. | | 6,380,423 B2 | 4/2002 | Banning et al. |
| 5,684,213 A | 11/1997 | Nemphos et al. | | 6,380,444 B1 | 4/2002 | Bjerrum et al. |
| 5,693,191 A | 12/1997 | Pividal et al. | | 6,395,945 B1 | 5/2002 | Randolph |
| 5,695,890 A | 12/1997 | Thompson et al. | | 6,403,840 B1 | 6/2002 | Zhou et al. |
| 5,698,747 A | 12/1997 | Godwin et al. | | 6,423,211 B1 | 7/2002 | Randolph et al. |
| 5,705,712 A | 1/1998 | Frey et al. | | 6,426,441 B1 | 7/2002 | Randolph et al. |
| 5,705,728 A | 1/1998 | Viswanathan et al. | | 6,426,442 B1 | 7/2002 | Ichikawa et al. |
| 5,705,729 A | 1/1998 | Huang | | 6,452,058 B1 | 9/2002 | Schweizer et al. |
| 5,708,246 A | 1/1998 | Camaioni et al. | | 6,455,650 B1 | 9/2002 | Lipian et al. |
| 5,720,858 A | 2/1998 | Noceti et al. | | 6,462,243 B1 | 10/2002 | Zhou et al. |
| 5,728,897 A | 3/1998 | Buysch et al. | | 6,465,696 B1 | 10/2002 | Zhou et al. |
| 5,728,905 A | 3/1998 | Clegg et al. | | 6,465,699 B1 | 10/2002 | Grosso |
| 5,734,073 A | 3/1998 | Chambers et al. | | 6,472,345 B2 | 10/2002 | Hintermann et al. |
| 5,741,949 A | 4/1998 | Mack | | 6,472,572 B1 | 10/2002 | Zhou et al. |
| 5,744,669 A | 4/1998 | Kalnes et al. | | 6,475,463 B1 | 11/2002 | Elomari et al. |
| 5,750,801 A | 5/1998 | Buysch et al. | | 6,475,464 B1 | 11/2002 | Rouleau et al. |
| 5,770,175 A | 6/1998 | Zones | | 6,479,705 B2 | 11/2002 | Murata et al. |
| 5,776,871 A | 7/1998 | Cothran et al. | | 6,482,997 B2 | 11/2002 | Petit-Clair et al. |
| 5,780,703 A | 7/1998 | Chang et al. | | 6,486,368 B1 | 11/2002 | Zhou et al. |
| 5,798,314 A | 8/1998 | Spencer et al. | | 6,495,484 B1 | 12/2002 | Holtcamp |
| 5,814,715 A | 9/1998 | Chen et al. | | 6,509,485 B2 | 1/2003 | Mul et al. |
| 5,817,904 A | 10/1998 | Vic et al. | | 6,518,474 B1 | 2/2003 | Sanderson et al. |
| 5,821,394 A | 10/1998 | Schoebrechts et al. | | 6,518,476 B1 | 2/2003 | Culp et al. |
| 5,847,224 A | 12/1998 | Koga et al. | | 6,525,228 B2 | 2/2003 | Chauvin et al. |
| 5,849,978 A | 12/1998 | Benazzi et al. | | 6,525,230 B2 | 2/2003 | Grosso |
| 5,866,735 A | 2/1999 | Cheung et al. | | 6,528,693 B1 | 3/2003 | Gandy et al. |
| 5,895,831 A | 4/1999 | Brasier et al. | | 6,538,162 B2 | 3/2003 | Chang et al. |
| 5,898,086 A | 4/1999 | Harris | | 6,540,905 B1 | 4/2003 | Elomari |
| 5,905,169 A | 5/1999 | Jacobson | | 6,545,191 B1 | 4/2003 | Stauffer |
| 5,906,892 A | 5/1999 | Thompson et al. | | 6,547,958 B1 | 4/2003 | Elomari |
| 5,908,963 A | 6/1999 | Voss et al. | | 6,548,040 B1 | 4/2003 | Rouleau et al. |
| 5,952,538 A | 9/1999 | Vaughn et al. | | 6,552,241 B1 | 4/2003 | Randolph et al. |
| 5,959,170 A | 9/1999 | Withers, Jr. | | 6,566,572 B2 | 5/2003 | Okamoto et al. |
| 5,969,195 A | 10/1999 | Stabel et al. | | 6,572,829 B2 | 6/2003 | Linkous et al. |
| 5,977,402 A | 11/1999 | Sekiguchi et al. | | 6,585,953 B2 | 7/2003 | Roberts et al. |
| 5,983,476 A | 11/1999 | Eshelman et al. | | 6,616,830 B2 | 9/2003 | Elomari |
| 5,986,158 A | 11/1999 | Van Broekhoven et al. | | 6,620,757 B2 | 9/2003 | McConville et al. |
| 5,994,604 A | 11/1999 | Reagen et al. | | 6,632,971 B2 | 10/2003 | Brown et al. |
| 5,998,679 A | 12/1999 | Miller | | 6,646,793 B2 | 10/2003 | Mul et al. |
| 5,998,686 A | 12/1999 | Clem et al. | | 6,646,102 B2 | 11/2003 | Boriack et al. |

| | | | | | | |
|---|---|---|---|---|---|---|
| 6,669,846 | B2 | 12/2003 | Perriello | 7,208,641 B2 | 4/2007 | Nagasaki et al. |
| 6,679,986 | B1 | 1/2004 | Da Silva et al. | 7,214,750 B2 | 5/2007 | McDonald et al. |
| 6,680,415 | B1 | 1/2004 | Gulotty, Jr. et al. | 7,220,391 B1 | 5/2007 | Huang et al. |
| 6,692,723 | B2 | 2/2004 | Rouleau et al. | 7,226,569 B2 | 6/2007 | Elomari |
| 6,710,213 | B2 | 3/2004 | Aoki et al. | 7,226,576 B2 | 6/2007 | Elomari |
| 6,713,087 | B2 | 3/2004 | Tracy et al. | 7,230,150 B2 | 6/2007 | Grosso et al. |
| 6,713,655 | B2 | 3/2004 | Yilmaz et al. | 7,230,151 B2 | 6/2007 | Martens et al. |
| 6,723,808 | B2 | 4/2004 | Holtcamp | 7,232,872 B2 | 6/2007 | Shaffer et al. |
| 6,727,400 | B2 | 4/2004 | Messier et al. | 7,238,846 B2 | 7/2007 | Janssen et al. |
| 6,753,390 | B2 | 6/2004 | Ehrman et al. | 7,244,795 B2 | 7/2007 | Agapiou et al. |
| 6,765,120 | B2 | 7/2004 | Weber et al. | 7,244,867 B2 | 7/2007 | Waycuilis |
| 6,797,845 | B1 | 9/2004 | Hickman et al. | 7,250,107 B2 | 7/2007 | Benazzi et al. |
| 6,797,851 | B2 | 9/2004 | Martens et al. | 7,250,542 B2 | 7/2007 | Smith, Jr. et al. |
| 6,821,924 | B2 | 11/2004 | Gulotty, Jr. et al. | 7,252,920 B2 | 8/2007 | Kurokawa et al. |
| 6,822,123 | B2 | 11/2004 | Stauffer | 7,253,327 B2 | 8/2007 | Janssens et al. |
| 6,822,125 | B2 | 11/2004 | Lee et al. | 7,253,328 B2 | 8/2007 | Stauffer |
| 6,825,307 | B2 | 11/2004 | Goodall | 7,265,193 B2 | 9/2007 | Weng et al. |
| 6,825,383 | B1 | 11/2004 | Dewkar et al. | 7,267,758 B2 | 9/2007 | Benazzi et al. |
| 6,831,032 | B2 | 12/2004 | Spaether | 7,268,263 B1 | 9/2007 | Frey et al. |
| 6,838,576 | B1 | 1/2005 | Wicki et al. | 7,271,303 B1 | 9/2007 | Sechrist et al. |
| 6,841,063 | B2 | 1/2005 | Elomari | 7,273,957 B2 | 9/2007 | Bakshi et al. |
| 6,852,896 | B2 | 2/2005 | Stauffer | 7,282,603 B2 | 10/2007 | Richards |
| 6,869,903 | B2 | 3/2005 | Matsunaga | 7,285,698 B2 | 10/2007 | Liu et al. |
| 6,875,339 | B2 | 4/2005 | Rangarajan et al. | 7,304,193 B1 | 12/2007 | Frey et al. |
| 6,878,853 | B2 | 4/2005 | Tanaka et al. | 7,342,144 B2 | 3/2008 | Kaizik et al. |
| 6,888,013 | B2 | 5/2005 | Paparatto et al. | 7,348,295 B2 | 3/2008 | Zones et al. |
| 6,900,363 | B2 | 5/2005 | Harth et al. | 7,348,464 B2 | 3/2008 | Waycuilis |
| 6,903,171 | B2 | 6/2005 | Rhodes et al. | 7,357,904 B2 | 4/2008 | Zones et al. |
| 6,909,024 | B1 | 6/2005 | Jones et al. | 7,361,794 B2 | 4/2008 | Grosso |
| 6,933,417 | B1 | 8/2005 | Henley et al. | 7,390,395 B2 | 6/2008 | Elomari |
| 6,946,566 | B2 | 9/2005 | Yaegashi et al. | 2002/0102672 A1 | 8/2002 | Mizrahi |
| 6,953,868 | B2 | 10/2005 | Boaen et al. | 2002/0198416 A1 | 12/2002 | Zhou et al. |
| 6,953,873 | B2 | 10/2005 | Cortright et al. | 2003/0004380 A1 | 1/2003 | Grumann |
| 6,956,140 | B2 | 10/2005 | Ehrenfeld | 2003/0065239 A1 | 4/2003 | Zhu |
| 6,958,306 | B2 | 10/2005 | Holtcamp | 2003/0069452 A1 | 4/2003 | Sherman et al. |
| 6,984,763 | B2 | 1/2006 | Schweizer et al. | 2003/0078456 A1 | 4/2003 | Yilmaz et al. |
| 7,001,872 | B2 | 2/2006 | Pyecroft et al. | 2003/0120121 A1 | 6/2003 | Sherman et al. |
| 7,002,050 | B2 | 2/2006 | Santiago Fernandez et al. | 2003/0125589 A1 | 7/2003 | Grosso |
| 7,011,811 | B2 | 3/2006 | Elomari | 2003/0166973 A1 | 9/2003 | Zhou et al. |
| 7,019,182 | B2 | 3/2006 | Grosso | 2004/0006246 A1 | 1/2004 | Sherman et al. |
| 7,026,145 | B2 | 4/2006 | Mizrahi et al. | 2004/0152929 A1 | 8/2004 | Clarke |
| 7,026,519 | B2 | 4/2006 | Santiago Fernandez et al. | 2004/0158107 A1 | 8/2004 | Aoki |
| 7,045,670 | B2 | 5/2006 | Johnson et al. | 2004/0158108 A1 | 8/2004 | Snoble |
| 7,049,388 | B2 | 5/2006 | Boriack et al. | 2004/0187684 A1 | 9/2004 | Elomari |
| 7,053,252 | B2 | 5/2006 | Boussand et al. | 2004/0188324 A1 | 9/2004 | Elomari |
| 7,057,081 | B2 | 6/2006 | Allison et al. | 2004/0220433 A1 | 11/2004 | Van Der Heide |
| 7,060,865 | B2 | 6/2006 | Ding et al. | 2005/0027084 A1 | 2/2005 | Clarke |
| 7,064,238 | B2 | 6/2006 | Waycuilis | 2005/0038310 A1 | 2/2005 | Lorkovic et al. |
| 7,064,240 | B2 | 6/2006 | Ohno et al. | 2005/0042159 A1 | 2/2005 | Elomari |
| 7,067,448 | B1 | 6/2006 | Weitkamp et al. | 2005/0148805 A1 | 7/2005 | Jones |
| 7,083,714 | B2 | 8/2006 | Elomari | 2005/0171393 A1 | 8/2005 | Lorkovic |
| 7,084,308 | B1 | 8/2006 | Stauffer | 2005/0192468 A1 | 9/2005 | Sherman et al. |
| 7,091,270 | B2 | 8/2006 | Zilberman et al. | 2005/0215837 A1 | 9/2005 | Hoffpauir |
| 7,091,387 | B2 | 8/2006 | Fong et al. | 2005/0234276 A1* | 10/2005 | Waycuilis .................. 585/310 |
| 7,091,391 | B2 | 8/2006 | Stauffer | 2005/0245772 A1 | 11/2005 | Fong |
| 7,094,936 | B1 | 8/2006 | Owens et al. | 2005/0245777 A1 | 11/2005 | Fong |
| 7,098,371 | B2 | 8/2006 | Mack et al. | 2005/0267224 A1 | 12/2005 | Herling |
| 7,105,710 | B2 | 9/2006 | Boons et al. | 2006/0025617 A1 | 2/2006 | Begley |
| 7,138,534 | B2 | 11/2006 | Forlin et al. | 2006/0100469 A1 | 5/2006 | Waycuilis |
| 7,141,708 | B2 | 11/2006 | Marsella et al. | 2006/0135823 A1 | 6/2006 | Jun |
| 7,145,045 | B2 | 12/2006 | Harmsen et al. | 2006/0138025 A1 | 6/2006 | Zones |
| 7,148,356 | B2 | 12/2006 | Smith, III et al. | 2006/0138026 A1 | 6/2006 | Chen |
| 7,148,390 | B2 | 12/2006 | Zhou et al. | 2006/0149116 A1 | 7/2006 | Slaugh |
| 7,151,199 | B2 | 12/2006 | Martens et al. | 2006/0229228 A1 | 10/2006 | Komon et al. |
| 7,161,050 | B2 | 1/2007 | Sherman et al. | 2006/0229475 A1 | 10/2006 | Weiss et al. |
| 7,169,730 | B2 | 1/2007 | Ma et al. | 2006/0270863 A1 | 11/2006 | Reiling |
| 7,176,340 | B2 | 2/2007 | Van Broekhoven et al. | 2006/0288690 A1 | 12/2006 | Elomari |
| 7,176,342 | B2 | 2/2007 | Bellussi et al. | 2007/0004955 A1 | 1/2007 | Kay |
| 7,182,871 | B2 | 2/2007 | Perriello | 2007/0078285 A1 | 4/2007 | Dagle |
| 7,193,093 | B2 | 3/2007 | Murray et al. | 2007/0100189 A1 | 5/2007 | Stauffer |
| 7,196,239 | B2 | 3/2007 | Van Egmond et al. | 2007/0129584 A1 | 6/2007 | Basset |
| 7,199,083 | B2 | 4/2007 | Zevallos | 2007/0142680 A1 | 6/2007 | Ayoub |
| 7,199,255 | B2 | 4/2007 | Murray et al. | 2007/0148067 A1 | 6/2007 | Zones |

| Publication No. | Date | Name | | Country | Number | Date |
|---|---|---|---|---|---|---|
| 2007/0148086 A1 | 6/2007 | Zones | | GB | 1172002 | 11/1969 |
| 2007/0149778 A1 | 6/2007 | Zones | | GB | 1212240 | 11/1970 |
| 2007/0149789 A1 | 6/2007 | Zones | | GB | 1233299 | 5/1971 |
| 2007/0149819 A1 | 6/2007 | Zones | | GB | 1253618 | 11/1971 |
| 2007/0149824 A1 | 6/2007 | Zones | | GB | 1263806 A | 2/1972 |
| 2007/0149837 A1 | 6/2007 | Zones | | GB | 1446803 | 8/1976 |
| 2007/0197801 A1 | 8/2007 | Bolk | | GB | 1542112 | 3/1979 |
| 2007/0197847 A1 | 8/2007 | Liu | | GB | 2095243 A | 9/1982 |
| 2007/0213545 A1 | 9/2007 | Bolk | | GB | 2095245 A | 9/1982 |
| 2007/0238905 A1 | 10/2007 | Arredondo | | GB | 2095249 A | 9/1982 |
| 2007/0238909 A1 | 10/2007 | Gadewar et al. | | GB | 2116546 A | 9/1982 |
| 2007/0276168 A1 | 11/2007 | Garel | | GB | 2120249 A | 11/1983 |
| 2007/0284284 A1 | 12/2007 | Zones | | GB | 2185754 A | 7/1987 |
| 2008/0171898 A1 | 7/2008 | Waycuilis | | GB | 2191214 A | 12/1987 |
| 2008/0183022 A1 | 7/2008 | Waycuilis | | JP | 2004-529189 | 9/2004 |
| 2008/0188697 A1 | 8/2008 | Lorkovic | | WO | 83/00859 | 3/1983 |

FOREIGN PATENT DOCUMENTS

| | | |
|---|---|---|
| CA | 1099656 | 4/1981 |
| CA | 1101441 | 5/1981 |
| CA | 1202610 | 4/1986 |
| CA | 2447761 AL | 11/2002 |
| CA | 2471295 AL | 7/2003 |
| CA | 2542857 | 5/2005 |
| CA | 2236126 | 8/2006 |
| CA | 2203115 | 9/2006 |
| CA | 2510093 | 12/2006 |
| EP | 0164798 A1 | 12/1985 |
| EP | 0418971 A1 | 3/1991 |
| EP | 0418974 A1 | 3/1991 |
| EP | 0418975 A1 | 3/1991 |
| EP | 0510238 A1 | 10/1992 |
| EP | 0526908 A2 | 2/1993 |
| EP | 0346612 B1 | 8/1993 |
| EP | 0560546 A1 | 9/1993 |
| EP | 0976705 A1 | 7/1998 |
| EP | 1186591 A2 | 3/2002 |
| EP | 1253126 A1 | 10/2002 |
| EP | 1312411 A2 | 5/2003 |
| EP | 1395536 | 3/2004 |
| EP | 1404636 | 4/2004 |
| EP | 1235769 B1 | 5/2004 |
| EP | 1435349 A2 | 7/2004 |
| EP | 1440939 A1 | 7/2004 |
| EP | 1474371 | 11/2004 |
| EP | 1235772 B1 | 1/2005 |
| EP | 1661620 A1 | 5/2006 |
| EP | 1760057 A1 | 3/2007 |
| EP | 1689728 B1 | 4/2007 |
| EP | 1808227 A1 | 7/2007 |
| EP | 1837320 A1 | 9/2007 |
| GB | 5125 | 2/1912 |
| GB | 156122 | 3/1922 |
| GB | 294100 | 6/1929 |
| GB | 363009 | 12/1931 |
| GB | 402928 | 12/1933 |
| GB | 474922 A | 11/1937 |
| GB | 536491 | 5/1941 |
| GB | 553950 | 6/1943 |
| GB | 586483 | 3/1947 |
| GB | 775590 | 5/1957 |
| GB | 793214 | 4/1958 |
| GB | 796048 | 6/1958 |
| GB | 796085 | 6/1958 |
| GB | 883256 | 11/1961 |
| GB | 950975 | 3/1964 |
| GB | 950976 | 3/1964 |
| GB | 991303 | 5/1965 |
| GB | 995960 | 6/1965 |
| GB | 1015033 | 12/1965 |
| GB | 1104294 | 2/1968 |
| GB | 1133752 | 11/1968 |
| WO | 85/04863 | 11/1985 |
| WO | 85/04867 | 11/1985 |
| WO | 90/08120 | 7/1990 |
| WO | 90/08752 | 8/1990 |
| WO | 91/18856 | 12/1991 |
| WO | 92/03401 | 3/1992 |
| WO | 92/12946 | 8/1992 |
| WO | 93/16798 | 9/1993 |
| WO | 96/22263 | 7/1996 |
| WO | 97/44302 | 11/1997 |
| WO | 98/12165 | 3/1998 |
| WO | 99/07443 | 2/1999 |
| WO | 00/07718 A1 | 2/2000 |
| WO | 00/09261 A1 | 2/2000 |
| WO | 01/14300 A1 | 3/2001 |
| WO | 01/38275 A1 | 5/2001 |
| WO | 01/44149 A1 | 6/2001 |
| WO | 02/094749 A1 | 11/2002 |
| WO | 02/094750 A1 | 11/2002 |
| WO | 02/094751 A2 | 11/2002 |
| WO | 02/094752 A1 | 11/2002 |
| WO | 03/000635 A1 | 1/2003 |
| WO | 03/002251 A2 | 1/2003 |
| WO | 03/018524 A1 | 3/2003 |
| WO | 03/020676 A1 | 3/2003 |
| WO | 03/022827 A2 | 3/2003 |
| WO | 03/043575 A2 | 5/2003 |
| WO | 03/051813 A1 | 6/2003 |
| WO | 03/062143 A1 | 7/2003 |
| WO | 03/062172 A2 | 7/2003 |
| WO | 03/078366 A1 | 9/2003 |
| WO | 2004/018093 A2 | 3/2004 |
| WO | 2004/067487 A2 | 8/2004 |
| WO | 2005/014168 A1 | 2/2005 |
| WO | 2005/019143 A1 | 3/2005 |
| WO | 2005/021468 A1 | 3/2005 |
| WO | 2005/035121 A2 | 4/2005 |
| WO | 2005/037758 A1 | 4/2005 |
| WO | 2005/054120 A2 | 6/2005 |
| WO | 2005/056525 A2 | 6/2005 |
| WO | 2005/058782 A1 | 6/2005 |
| WO | 2005/090272 A1 | 9/2005 |
| WO | 2005/095310 A2 | 10/2005 |
| WO | 2005/105709 A1 | 11/2005 |
| WO | 2005/105715 A1 | 11/2005 |
| WO | 2005/110953 A1 | 11/2005 |
| WO | 2005/113437 A1 | 12/2005 |
| WO | 2005/113440 A1 | 12/2005 |
| WO | 2006/007093 A1 | 1/2006 |
| WO | 2006/015824 A1 | 2/2006 |
| WO | 2006/019399 A2 | 2/2006 |
| WO | 2006/020234 A1 | 2/2006 |
| WO | 2006/039213 A1 | 4/2006 |
| WO | 2006/039354 A2 | 4/2006 |
| WO | 2006/043075 A1 | 4/2006 |
| WO | 2006/1036293 A1 | 4/2006 |
| WO | 2006/053345 A1 | 5/2006 |

| | | |
|---|---|---|
| WO | 2006-067155 A2 | 6/2006 |
| WO | 2006/067188 A1 | 6/2006 |
| WO | 2006/067190 A1 | 6/2006 |
| WO | 2006/067191 A1 | 6/2006 |
| WO | 2006/067192 A1 | 6/2006 |
| WO | 2006/067193 A1 | 6/2006 |
| WO | 2006/069107 A2 | 6/2006 |
| WO | 2006/071354 A1 | 7/2006 |
| WO | 2006/076942 A1 | 7/2006 |
| WO | 2006/083427 A2 | 8/2006 |
| WO | 2006-100312 A2 | 9/2006 |
| WO | 2006/104909 A2 | 10/2006 |
| WO | 2006/104914 A1 | 10/2006 |
| WO | 2006/111997 A1 | 10/2006 |
| WO | 2006/113205 A2 | 10/2006 |
| WO | 2006/118935 A2 | 11/2006 |
| WO | 2007/001934 A2 | 1/2007 |
| WO | 2007/017900 A2 | 2/2007 |
| WO | 2007/044139 A1 | 4/2007 |
| WO | 2007/046986 A2 | 4/2007 |
| WO | 2007/050745 A1 | 5/2007 |
| WO | 2007/07104 A1 | 6/2007 |
| WO | 2007/079038 A2 | 7/2007 |
| WO | 2007/091009 A2 | 8/2007 |
| WO | 2007/094995 A2 | 8/2007 |
| WO | 2007/107031 A1 | 9/2007 |
| WO | 2007/114479 A1 | 10/2007 |
| WO | 2007111997 A2 | 10/2007 |
| WO | 2007/125332 A1 | 11/2007 |
| WO | 2007/130054 A1 | 11/2007 |
| WO | 2007/130055 A1 | 11/2007 |
| WO | 2007/141295 A1 | 12/2007 |
| WO | 2007/142745 A1 | 12/2007 |

OTHER PUBLICATIONS

U.S. Appl. No. 60/559,844, filed Apr. 6, 2004, inventor Sherman et al.
U.S. Appl. No. 60/765,115, filed Feb. 3, 2006, inventor Gadewar et al.
JLM Technology Ltd.; "The Miller GLS Technology for Conversion of Light Hydrocarbons to Alcohols"; New Science for the Benefit of Humanity; May 31, 2000; pp. 1-10.
Jaumain, Denis and Su, Bao-Lian; "Direct Catalytic Conversion of Chloromethane to Higher Hydrocarbons Over Various Protonic and Cationic Zeolite Catalysts as Studied by in-situ FTIR and Catalytic Testing"; 2000; pp. 1607-1612; Studies in Surface Science and Catalysis 130; Elsevier Science B.V.
Taylor, Charles E.; "Conversion of Substituted Methanes Over ZSM-Catalysts"; 2000; pp. 3633-3638; Studies in Surface Science and Catalysis 130; Elsevier Science B.V.
ZSM-5 Catalyst; http://chemelab.ucsd.edu/methanol/memos/ZSM-5.html; Nov. 06, 2003; p. 1.
Final Report; "Abstract"; http://chemelab.ucsd.edu/methanol/memos/final.html; May 9, 2004; pp. 1-7.
Driscoll, Daniel J.; "Direct Methane Conversion"; Federal Energy Technology Center, U.S. Department of Energy; M970779; 2001; pp. 1-10.
Olah et al.; "Selective Monohalogenation of Methane over Supported Acid or Platinum Metal Catalysts and Hydrolysis of Methyl Halides . . . "; J. American Chemical Society 1985, vol. 107; 0002-7863/85/1507-7097$01.50/0; pp. 7097-7105.
Murray et al.; "Conversion of Methyl Halides to Hydrocarbons on Basic Zeolites: a Discovery by in Situ NMR"; J. American Chemical Society 1993, vol. 115; pp. 4732-4741.
Lorkovic et al.; "A Novel Integrated Process for the Functionalization of Methane and Ethane: Bromine as Mediator", Catalysis Today 98; 2004; pp. 317-322.
Lorkovic et al.; "C1 Oxidative Coupling via Bromine Activation and Tandem Catalytic Condensation over CaO/ Zeolite Composites II . . . "; Catalysis Today 98; 2004; pp. 589-594.
Olah et al.; "Antimony Pentafluoride/Graphite Catalyzed Oxidative Conversion of Methyl Halides with Copper Oxides (or Copper/Oxygen) to Dimethyl Ether"; J. Org. Chem. 1990, 55; 1990 American Chemical Society; pp. 4289-4293.

Taylor, Charles E. et al.; "Direct Conversion of Methane to Liquid Hydrocarbons Through Chlorocarbon Intermediates"; 1988 Elsevier Science Publishers B.V. Amsterdam, Netherlands; pp. 483-489.
Chang, Clarence D. et al.; "The Conversion of Methanol and Other O-Compounds to Hydrocarbons over Zeolite Catalysts"; Journal of Catalysis 47; 1977; Academic Press, Inc.; pp. 249-259.
Zhou, Xiao-Ping et al.; "An Integrated Process for Partial Oxidation of Alkanes"; Chem. Commun. 2003; The Royal Society of Chemistry 2003; pp. 2294-2295.
Sun, Shouli et al.; "A General Integrated Process for Synthesizing Olefin Oxides"; Chem. Commun. 2004; The Royal Society of Chemistry 2004; pp. 2100-2101.
Lorkovic, Ivan M. et al.; "C1 Oxidative Coupling via Bromine Activation and Tandem Catalytic Condensation and Neutralization over CaO/Zeolite Composites II . . . "; Catalysis Today 98; 2004; pp. 589-594.
Yilmaz, Aysen et al.; "Bromine Mediated Partial Oxidation of Ethane over Nanostructured Zirconia Supported Metal Oxide/Bromide"; Microporous and Mesoporous Materials, 79; 2005; pp. 205-214.
Taylor, Charles E.; "PETC's On-Site Natural Gas Conversion Efforts"; Preprints of the Fuel Division, 208th National Meeting of the American Chemical Society, 39 (4); 1994; pp. 1228-1232.
Ione et al.; "Syntheses of Hydrocarbons from Compounds Containing One Carbon Atom Using Bifunctional Zeolite Catalysts"; Solid Fuel Chemistry (Khimiya Tverdogo Topliva); 1982; pp. 29-43; vol. 16, No. 6; Allerton Press. Inc.
Olah, George A. et al.; "Hydrocarbons Through Methane Derivatives"; Hydrocarbon Chemistry; 1995; pp. 89-90; John Wiley & Sons, Inc.
Akhrem, Irena S. et al.; "Ionic Bromination of Ethane and Other Alkanes (Cycloalkanes) with Bromine Catalyzed by the Polyhalomethane-2AlBr3 Aprotic Organic Superacids Under Mild Conditions"; Tetrahedron Letters, vol. 36, No. 51, 1995; pp. 9365-9368; Pergamon; Great Britain.
Smirnov, Vladimir V. et al.; "Selective Bromination of Alkanes and Arylalkanes with CBr4"; Mendeleev Commun. 2000; pp. 175-176.
Olah, George A.; "Electrophilic Methane Conversion"; Acc. Chem. Res. 1987, 20; pp. 422-428; American Chemical Society, Loker Hydrocarbon Research Institute and Dept. Of Chemistry; University of Southern California.
Olah, George A. et al.; "Antimony Pentafluoride/Graphite Catalyzed Oxidative Carbonylation of Methyl Halides with Carbon Monoxide and Copper Oxides (or Copper/Oxygen) to Methyl Acetate"; J. Org. Chem. 1990, 55; pp. 4293-4297; Loker Hydrocarbon Research Institute and Dept. Of Chemistry; University of Southern California.
Bagno, Alessandro et al.; "Superacid-Catalyzed Carbonylation of Methane, Methyl Halides, Methyl Alcohol, and Dimethyl Ether to Methyl Acetate and Acetic Acid"; J. Org. Chem. 1990, 55; pp. 4284-4289; Loker Hydrocarbon Research Institute; University of Southern California.
Olah, George A. et al.; "Onium Ylide Chemistry. 1. Bifunctional Acid-Base-Catalyzed Conversion of Heterosubstituted Methanes into Ethylene and Derived Hydrocarbons. The Onium Ylide Mechanism of the C1-C2 Conversion"; J. Am. Chem. Soc. 1984, 106; pp. 2143-2149.
Mochida, Isao et al.; "The Catalytic Dehydrohalogenation of Haloethanes on Solid Acids and Bases"; Bulletin of the Chemical Society of Japan, vol. 44; 1971; pp. 3305-3310.
Richards, Ryan et al.; "Nanocrystalline Ultra High Surface Area Magnesium Oxide as a Selective Base Catalyst"; Scripta Materialia, 44; 2001; pp. 1663-1666; Elsevier Science Ltd.
Sun, Naijian et al.; "Nanocrystal Metal Oxide—Chlorine Adducts: Selective Catalysts for Chlorination of Alkanes"; J. Am. Chem. Soc. 1999, 121; pp. 5587-5588; American Chemical Society.
Mishakov, Ilya V. et al.; "Nanocrystalline MgO as a Dehydrohalogenation Catalyst"; Journal of Catalysis 206; 2002; pp. 40-48; Elsevier Science, USA.
Wagner, George W. et al.; "Reactions of VX, GD, and HD with Nanosize CaO: Autocatalytic Dehydrohalogenation of HD"; J. Phys. Chem. B 2000, 104; pp. 5118-5123; 2000 American Chemical Society.
Fenelonov, Vladimir B. et al.; "Changes in Texture and Catalytic Activity of Nanocrystalline MgO during Its Transformation to MgCl2 in the Reaction with 1-Chlorobutane"; J. Phys. Chem. B 2001, 105; pp. 3937-3941; 2001 American Chemical Society.
http://webbook.nist.govi; "Welcome to the NIST Chemistry WebBook"; 2005; U.S. Secretary of Commerce on Behalf of the United States of America.
Claude, Marion C. et al.; "Monomethyl-Branching of Long n-Alkanes in the Range from Decane to Tetracosane on Pt/H-ZSM-22 Bifunctional Catalyst"; Journal of Catalysis 190; 2000; pp. 39-48.
Thomas, J. M. et al.; "Synthesis and Characterization of a Catalytically Active Nickel-Silicoaluminophosphate Catalyst for the Conversion of Methanol to Ethene"; Chem. Mater.; 1991, 3; pp. 667-672; 1991 American Chemical Society.
Thomas, John Meurig et al.; "Catalytically Active Centres in Porous Oxides: Design and Performance of Highly Selective New Catalysts"; Chem. Commun.; 2001; pp. 675-687.
Lorkovic, Ivan et al.; "C1 Coupling via Bromine Activation and Tandem Catalytic Condensation and Neutralization over CaO/Zeolite Composites"; Chem. Commun., 2004; pp. 566-567.
Tamura, Masuhiko et al.; "The Reactions of Grignard Reagents with Transition Metal Halides: Coupling, Disproportionation, and Exchange with Olefins"; Bulletin of the Chemical Society of Japan, vol. 44.; Nov. 1971; pp. 3063-3073.
Weissermel, Klaus et al.; "Industrial Organic Chemistry"; 3rd Edition 1997. pp. 160-162, and 208.
Abstract of BE812868, Aromatic hydrocarbons prodn. from chlorinated hydrocarbons, Publication date: Sep. 27, 1974, esp@cenet database - worldwide.
Abstract of BE814900, Volatile aramatic cpds. prodn., Publication date: Sep. 2, 1974, esp@cenet database - worldwide.
Abstract of CN1199039, Pentanol and its production process, Publication date: Nov. 18, 1998, Inventor: Kailun, esp@cenet database - worldwide.
Abstract of on 1210847, Process for producing low carbon alcohol by directly hydrating low carbon olefines, Publication date: Mar. 3, 1999, Inventor: Zhenguo et al., esp@cenet database - worldwide.
Abstract of CN1321728, Method for preparing aromatic hydrocarbon and hydrogen gas by using low-pressure gas, Publication date: Nov. 14, 2001, Inventor: Jie et al., esp@cenet database - worldwide.
Abstract of CN1451721, Process for non-catalytic combustion deoxidizing coal mine gas for producing methanol, Publication date: Oct. 29, 2003, Inventor: Pengwan et al., esp@cenet database - worldwide.
Abstract of CN1623969, Method for preparing 1, 4-benzene dimethanol, Publication date: Jun. 8, 2005, Inventor: Jiarong et al., esp@cenet database - worldwide.
Abstract of CN1657592, Method for converting oil to multiple energy fuel product, Publication date: Aug. 24, 2005, Inventor: Li, esp@cenet database - worldwide.
Abstract of CN1687316, Method for producing biologic diesel oil from rosin, Publication date: Oct. 26, 2005, Inventor: Jianchun et al., esp@cenet database - worldwide.
Abstract of CN1696248, Method for synthesizing biologic diesel oil based on ion liquid, Publication date: Nov. 16, 2005, Inventor: Sun, esp@cenet database - worldwide.
Abstract of CN1699516, Process for preparing bio-diesel-oil by using microalgae fat, Publication date: Nov. 23, 2005, Inventor: Miao, esp@cenet database - worldwide.
Abstract of CN1704392, Process for producing alkylbenzene, Publication date: Dec. 7, 2005, Inventor: Gao, esp@cenet database - worldwide.
Abstract of CN1724612, Biological diesel oil catalyst and method of synthesizing biological diesel oil using sai catalyst, Publication date: Jan. 25, 2006, Inventor: Gu, esp@cenet database - worldwide.
Abstract of CN1986737, Process of producing biodiesel oil with catering waste oil, Publication date: Jun. 27, 2007, Inventor: Chen, esp@cenet database - worldwide.
Abstract of CN100999680, Esterification reaction tech, of preparing biodiesel by waste oil, Publication date: Jul. 18, 2007, Inventor: Weiming, esp@cenet database - worldwide.
Abstract of CN101016229, Refining method for bromomeoamyl alcohol, Publication date: Aug. 15, 2007, Inventor: Tian, esp@cenet database - worldwide. .

Abstract of DE3209964, Process for the preparation of chlorinated hydrocarbons, Publication date: Nov. 11, 1982, Inventor: Pyke et al., esp@cenet database - worldwide.
Abstract of DE3210196, Process for the preparation of a monochlorinated olefin, Publication date: Jan. 5, 1983, Inventor: Pyke et al., esp@cenet database - worldwide.
Abstract of DE3226028, Process for the preparation of monochlorinated olefin, Publication date: Feb. 3, 1983, Inventor: Pyke et al., esp@cenet database - worldwide.
Abstract of DE3334225, Process for the preparation of 1, 2-dichloroethane, Publication date: Apr. 4, 1985, Inventor: Hebgen et al., esp@cenet database - worldwide.
Abstract of DE4232056, 2,5-Di:methyl-hexane-2, 5-di:ol continuous prodn. from tert. butanol - by oxidative dimerisation in two phase system with vigorous stirring, using aq. phase with specified density to facilitate phase sepn., Publication date: Mar. 31, 1994, Inventor: Gnann et al., esp@cenet database - worldwide.
Abstract of DE4434823, Continuous prodn. Of hydroxy-benzyl alkyl ether, Publication date: Apr. 4, 1996, Inventor: Stein et al., esp@cenet database - worldwide.
Abstract of FR2692259, Aromatisation of 2-4C hydrocarbons - using a fixed-mobile-catalytic bed process, Publication date: Dec. 17, 1993, Inventor: Alario et al., esp@cenet database - worldwide.
Abstract of FR2880019, Manufacturing 1, 2-dichloroethane, comprises cracking core hydrocarbonated source, separating into fractions, sending into chlorination reaction chamber and oxychlorination reaction chamber and separating from chambers, Publication date: Jun. 30, 2006, Inventor: Strebelle et al., esp@cenet database - worldwide.
Abstract of FR2883870, Formation of 1, 2-dichloroethane useful in manufacture of vinyl chloride involves subjecting mixture of cracking products obtained by cracking of hydrocarbon source, to a succession of aqueous quenching, alkaline washing, and oxidation steps, Publication date: Oct. 6, 2006, Inventor: Balthasart et al., esp@cenet database - worldwide.
Abstract of FR2883871, Preparing 1, 2-dichloroethane comprises cracking hydrocarbon to form mixture, sending mixture into storage reservoir, supplying mixture into chlorination and/or oxychloration reactor, and separating 1, 2- dichloroethane from reactor, Publication date: Oct. 6, 2006, Inventor: Balthasart et al., esp@cenet database - worldwide.
Abstract of IT1255246, Process for the preparation of dinitrodiphenylmethanes, Publication date: Oct. 20, 1995, Applicant: Enichem Spa et al., esp@cenet database - worldwide.
Abstract of IT1255358, Process for the synthesis of 1, 4-butanediol, Publication date: Oct. 31, 1995, Inventor: Marco, esp@cenet database - worldwide.
Abstract of JP2142740, Production of fluoroalcohol, Publication date: May 31, 1990, Inventor: Tsutomu et al., esp@cenet database - worldwide.
Abstract of JP2144150, Chemical process and catalyst used therefore, Publication date: Jun. 1, 1990, Inventor: Deidamusu et al., esp@cenet database - worldwide.
Abstract of JP4305542, Production of halogenated hydrocarbon compounds, Publication date: Oct. 28, 1992, Inventor: Shinsuke et al., esp@cenet database - worldwide.
Abstract of JP6172225, Method for fluorinating halogenated hydrocarbon, Publication date: Jun. 21, 1994, Inventor: Takashi et al., esp@cenet database - worldwide.
Abstract of JP6206834, Production of tetrachloroethanes, Publication date: Jul. 26, 1994, Inventor: Toshiro et al., esp@cenet database - worldwide.
Abstract of JP8266888, Method for decomposing aromatic halogen compound, Publication date: Oct. 15, 1996, Inventor: Yuuji et al., esp@cenet database - worldwide.
Abstract of JP2001031605, Production of 3-hydroxy-1-cycloalkene, Publication date: Feb. 6, 2001, Inventor: Hideo et al, esp@cenet database - worldwide.
Abstract of JP2004075683, Method for producing optically active halogenohydroxypropyl compound and glycidyl compound, Publication date: Mar. 11, 2004, Inventor: Keisuke et al., esp@cenet database - worldwide.

Abstract of JP2004189655, Method for fluorinating with microwave, Publication date: Jul. 8, 2004, Inventor: Masaharu et al., esp@cenet database - worldwide.

Abstract of JP2005075798, Method for Producing adamantyl ester compound, Publication date: Mar. 24, 2005, Inventor: Norihiro et al., esp@cenet database - worldwide.

Abstract of JP2005082563, Method for producing 1, 3-adamantanediol, Publication date: Mar. 31, 2005, Inventor: Norihiro et al., esp@cenet database - worldwide.

Abstract of JP2005145977, Process for catalytically oxidizing olefin and cycloolefin for the purpose of forming enol, olefin ketone, and epoxide, Publication date: Jun. 9, 2005, Inventor: Cancheng et al., esp@cenet database - worldwide.

Abstract of JP2005254092, Method of manufacturing alkynes, Publication date: Sep. 22, 2005, Inventor: Shirakawa Eiji, esp@cenet database - worldwide.

Abstract of JP2006151892, Preparation method of alcohol derivative, Publication date: Jun. 15, 2006, Inventor: Baba Akio et al., esp@cenet database - worldwide.

Abstract of JP2006152263, Organic-inorganic hybrid-type mesoporous material, method for producing the same, and solid catalyst, Publication date: Jun. 15, 2006, Inventor: Junko et al., esp@cenet database - worldwide.

Abstract of JP2006193473, Aryl polyadamantane derivative having carboxy or acid anhydride group and method for producing the same, Publication date: Jul. 27, 2006, Inventor: Yasuto et al., esp@cenet database-worldwide.

Abstract of JP2006231318, Phosphorus containing macromolecule immobilizing palladium catalyst and method for using the same, Publication date: Sep. 7, 2006, Inventor: Osamu et al., esp@cenet database - worldwide.

Abstract of JP2006263567, Optical resolution method of optical isomer and optical resolution device, Publication date: Oct. 5, 2006, Inventor: Yoshikazu et al., esp@cenet database - worldwide.

Abstract of JP2006265157, Method for catalytically activating silicated nucleating agent using phosphazene base, Publication date: Oct. 5, 2006, Inventor: Yoshinori et al., esp@cenet database - worldwide.

Abstract of JP2006306758, Method for producing biaryl compound, Publication date: Nov. 9, 2006, Inventor: Yuji et al., esp@cenet database - worldwide.

Abstract of JP2007001942, Production method of para-xylene, Publication date: Jan. 11, 2007, Inventor: Kazuyoshi, esp@cenet database - worldwide.

Abstract of JP2007015994, Method for synthesizing organic compound in ultra high rate under high temperature and high pressure water, and system of high temperature and high pressure reaction, Publication date: Jan. 25, 2007, Inventor: Hajime et al., esp@cenet database - worldwide.

Abstract of JP2007045756, Hydrogenation method using diaphragm type hydrogenation catalyst, hydrogenation reaction apparatus and diaphragm type hydrogenation catalyst, Publication date: Feb. 2, 2007, Inventor: Shuji et al., esp@cenet database - worldwide.

Abstract of JP2007061594, Method for decomposing organohalogen compound and mobile decomposition system, Publication date: Mar. 15, 2007, Inventor: Koichi et al., esp@cenet database - worldwide.

Abstract of JP2007099729, Method for producing alpha-methylstyrene or cumene, Publication date: Apr. 19, 2007, Inventor: Toshio, esp@cenet database - worldwide.

Abstract of RO119778, Process for preparing perchloroethylene, Publication date: Mar. 30, 2005, Inventor: Horia et al., esp@cenet database - worldwide.

Abstract of WO0105737, Method for preparing a carboxylic acid, Publication date: Jan. 25, 2001, Inventor: Pascal et al., esp@cenet database - worldwide.

Abstract of WO0105738, Method for preparing a carboxylic acid, Publication date: Jan. 25, 2001, Inventor: Pascal et al., esp@cenet database - worldwide.

Abstract of WO2004092099, Method for producing cyclic enols, Publication date: Oct. 28, 2004, Inventor: Marko et al., esp@cenet database - worldwide.

Abstract of WO2006063852, Electroluminescent polymers and use thereof, Publication date: Jun. 22, 2006, Inventor: Arne et al., esp@cenet database - worldwide.

Abstract of WO2006136135, Method for decarboxylating C-C cross-linking of carboxylic acids with carbon electrophiles, Publication date: Dec. 28, 2006, Inventor: Goossen Lukas et al., esp@cenet database - worldwide.

Abstract of WO2007028761, Method for chlorinating alcohols, Publication date: Mar. 15, 2007, Inventor: Rohde et al., esp@cenet database - worldwide. @.

Abstract of WO2007128842, Catalytic transalkylation of dialkyl benzenes, Publication date: Nov. 15, 2007, Inventor: Goncalvesalmeida et al., esp@cenet database - worldwide. 2.

Abstract of WO2007137566, Method for catalytic conversion of organic oxygenated compounds from biomaterials, Publication date: Dec. 6, 2007, Inventor: Reschetilowski, esp@cenet database - worldwide.

Abstract of WO9721656, Method for making fluoroalkanols, Publication date: Jun. 19, 1997, Inventor: Gillet, esp@cenet database - worldwide.

Abstract of WO9950213, Method for producing dialkyl ethers, Publication date: Oct. 7, 1999, Inventor: Falkowski Juergen et al., esp@cenet database - worldwide.

Abstract of EP0039471, Process for the preparation of 2-chloro-1,1,1,2,3,3,3-heptafluoropropane, Publication date: Nov. 11, 1981, Inventor: Von Halasz, esp@cenet database - worldwide.

Abstract of EP0101337, Process for the production of methylene chloride, Publication date: Feb. 22, 1984, Inventor: Olah et al., esp@cenet database - worldwide.

Abstract of EP0407989, Method for the production of 1,1,1-trifluoro-2,2-dichloroethane by photochlorination, Publication date: Jan. 16, 1991, Inventor: Cremer et al., esp@cenet database - worldwide.

Abstract of EP0442258, Process for the preparation of a polyunsaturated olefin, Publication date: Aug. 21, 1991, Inventor: Gaudin et al., esp@cenet database - worldwide.

Abstract of EP0465294, Process for the preparation of unsaturated bromides, Publication date: Jan. 8, 1992, Inventor: Decaudin et al., esp@cenet database - worldwide.

Abstract of EP0549387, Synthesis of n-perfluorooctylbromide, Publication date: Jun. 30, 1993, Inventor: Drivon et al., esp@cenet database - worldwide.

Abstract of EP0850906, Process and apparatus for the etherification of olefinic hydrocarbon feedstocks, Publication date: Jul. 1, 1998, Inventor: Masson, esp@cenet database - worldwide.

Abstract of EP0858987, Process for the conversion of lighter alkanes to higher hydrocarbons, Publication date: Aug. 19, 1998, Inventor: Amariglio et al., esp@cenet database - worldwide.

Abstract of EP0235110, Process for the stabilization of silicalite catalysts, Publication date: Sep. 2, 1987, Inventor: Debras et al., esp@cenet database - worldwide.

U.S. Office Action from U.S. Appl. No. 10/826,885 dated Oct. 31, 2005.

U.S. Office Action from U.S. Appl. No. 10/826,885 dated Apr. 19, 2006.

U.S. Office Action from U.S. Appl. No. 10/826,885 dated Jul. 27, 2006.

U.S. Office Action from U.S. Appl. No. 10/826,885 dated Nov. 02, 2006.

U.S. Office Action from U.S. Appl. No. 10/826,885 dated Jan. 24, 2007.

U.S. Office Action from U.S. Appl. No. 11/101,886 dated Jan. 24, 2007.

U.S. Office Action from U.S. Appl. No. 11/254,438 dated Jan. 24, 2007.

U.S. Office Action from U.S. Appl. No. 11/254,438 dated Nov. 01, 2007.

* cited by examiner

CONTINUOUS PROCESS FOR CONVERTING NATURAL GAS TO LIQUID HYDROCARBONS

CROSS-REFERENCE TO RELATED APPLICATION

This application is based on and claims priority of U.S. Provisional Patent Application No. 60/765,115, filed Feb. 3, 2006, the entire contents of which are incorporated by reference herein.

FIELD OF THE INVENTION

This invention generally relates to carbon-carbon coupling and, more particularly, to methods for converting hydrocarbon feedstocks into useful products.

BACKGROUND OF THE INVENTION

Scientists have long sought efficient ways to convert methane and other hydrocarbons into longer chain hydrocarbons, olefins, aromatic hydrocarbons, and other products. CH bond activation has been the focus of intense research for decades, with mixed results. More efficient processes could create value in a number of ways, including facilitating the utilization of remotely located hydrocarbon feedstocks (such as stranded natural gas) through conversion into more easily transportable and useful fuels and feedstocks, and allowing the use of inexpensive feedstocks (e.g., methane and other light hydrocarbons) for end products often made from higher hydrocarbons.

U.S. Pat. No. 6,525,230 discloses methods of converting alkanes to other compounds using a "zone reactor" comprised of a hollow, unsegregated interior defining first, second, and third zones. Oxygen reacts with metal bromide in the first zone to provide bromine; bromine reacts with the alkane in the second zone to form alkyl bromide and hydrogen bromide; and the alkyl bromide reacts with metal oxide in the third zone to form the corresponding product. In one embodiment, the flow of gases through the reactor is reversed to convert the metal oxide back to metal bromide and to convert the metal bromide back to the metal oxide. The reactor is essentially operated in a cyclic mode.

U.S. Pat. No. 6,452,058 discloses an oxidative halogenation process for producing alkyl halides from an alkane, hydrogen halide, and, preferably, oxygen, using a rare earth halide or oxyhalide catalyst. The alternative of using molecular halogen is also mentioned. Other patents, such as U.S. Pat. Nos. 3,172,915, 3,657,367, 4,769,504, and 4,795,843, disclose the use of metal halide catalysts for oxidative halogenation of alkanes. Oxidative halogenation, however, has several disadvantages, including the production of perhalogenated products and an unacceptable quantity of deep oxidation products (CO and $CO_2$).

Three published U.S. patent applications, Pub. Nos. 2005/0234276, 2005/0234277, and 2006/0100469 (each to Waycuilis), describe bromine-based processes for converting gaseous alkanes to liquid hydrocarbons. Several basic steps are described, including (1) reacting bromine with alkanes to produce alkyl bromides and hydrobromic acid (bromination), (2) reacting the alkyl bromide and hydrobromic acid product with a crystalline alumino-silicate catalyst to form higher molecular weight hydrocarbons and hydrobromic acid (coupling), (3) neutralizing the hydrobromic acid by reaction with an aqueous solution of partially oxidized metal bromide salts (as metal oxides/oxybromides/bromides) to produce a metal bromide salt and water in an aqueous solution, or by reaction of the hydrobromic acid with air over a metal bromide catalyst, and (4) regenerating bromine by reaction of the metal bromide salt with oxygen to yield bromine and an oxidized salt. Potential drawbacks of the processes include low methane conversions; short space-times and the resulting potential for less than 100% bromine conversion; wasteful overbromination of ethane, propane, and higher alkanes, resulting in the formation of dibromomethane and other polybrominated alkanes, which will likely form coke under the disclosed reaction conditions; comparatively low alkyl bromide conversions; the need to separate the hydrocarbon product stream from an aqueous hydrohalic acid stream; and inadequate capture of halogen during the regeneration of the catalyst to remove halogen-containing coke. In addition, the proposed venting of this bromine-containing stream is both economically and environmentally unacceptable.

The Waycuilis process also apparently requires operation at relatively low temperatures to prevent significant selectivity to methane. The likely result would be incomplete conversion of alkyl bromide species and, because the described process relies on stream splitting to recover products, a considerable amount of unconverted alkyl bromides would likely leave the process with the products. This represents an unacceptable loss of bromine (as unconverted methyl bromide) and a reduced carbon efficiency.

The neutralization of hydrobromic acid by reaction with an aqueous solution of partially oxidized metal bromide salts and subsequent reaction of the metal bromide salts formed with oxygen to yield bromine and an oxidized salt, as disclosed by Waycuilis, also has a number of disadvantages. First, any carbon dioxide present will form carbonates in the slurry, which will not be regenerable. Second, the maximum temperature is limited due to pressure increases which are intolerable above approximately 200° C., thus preventing complete recovery of halogen. Third, although the use of redox-active metal oxides (e.g., oxides of V, Cr, Mn, Fe, Co, Ce, and Cu) will contribute to molecular bromine formation during the neutralization of hydrobromic acid, incomplete HBr conversion due to the use of a solid bromide salt will in turn result in a significant loss of bromine from the system (in the water phase). Provided an excess of air was used, the bromide salt might eventually be converted to the oxide form, stopping any further loss of HBr in the water discard.

To separate water from bromine, Waycuilis discloses the use of condensation and phase separation to produce semidry liquid bromine and a water/bromine mixture. Other means for separating water from bromine, such as using an inert gas to strip the bromine from the water phase or using adsorption-based methods have also been proposed by others; however, such methods are minimally effective and result in a significant overall loss of halogen.

The prior art oxychlorination process first removes the water from HCl (a costly step) and then reacts the HCl with oxygen and hydrocarbon directly. Oxychlorination processes rely on the separation of HCl from the unreacted alkanes and higher hydrocarbon products by using water absorption, and subsequent recovery of anhydrous HCl from the aqueous hydrochloric acid. U.S. Pat. No. 2,220,570 discloses a process and apparatus for the absorption of HCl in water where the heat of absorption is dissipated by contacting the HCl gas with ambient air, and also by the vaporization of water. A process for producing aqueous hydrochloric acid with a concentration of at least 35.5 wt % by absorbing gaseous HCl in water is disclosed in U.S. Pat. No. 4,488,884. U.S. Pat. No. 3,779,870 teaches a process for the recovery of anhydrous HCl gas by extractive distillation using a chloride salt. U.S.

Pat. No. 4,259,309 teaches a method for producing gaseous HCl from dilute aqueous HCl using an amine together with an inert water-immiscible solvent.

Although researchers have made some progress in the search for more efficient CH bond activation pathways for converting natural gas and other hydrocarbon feedstocks into fuels and other products, there remains a tremendous need for a continuous, economically viable, and more efficient process.

SUMMARY OF THE INVENTION

In one aspect of the invention, a continuous process for converting methane, natural gas, and other hydrocarbon feedstocks into one or more higher hydrocarbons or olefins is provided. In one embodiment of the invention, the process includes the steps of alkane halogenation, "reproportionation" of polyhalogenated compounds to increase the amount of monohalides that are formed, oligomerization (C-C coupling) of alkyl halides (and optionally, olefins) to form higher carbon number products, separation of products from hydrogen halide, continuous regeneration of halogen, and separation and recovery of molecular halogen from water.

The invention exploits the discovery that, following consumption of substantially all of the molecular halogen in an alkane halogenation reactor, polyhalogenated hydrocarbons that are formed can be reacted with unhalogenated alkanes to improve the overall yield of monohalides, which react in later process steps more efficiently—and form more desirable products—than polyhalogenated species. After the initial alkane halogenation reaction, which consumes substantially all of the molecular halogen, additional halogenation is accomplished by transfer of halogen from polyhalogenated alkanes to unhalogenated alkanes, thereby reducing carbon loss and coke formation. For example, dibromomethane can be reproportionated with methane to form methyl bromide, and dibromomethane can be reproportionated with ethane or propane to form ethyl bromide and ethylene and/or propyl bromide and propylene. Although not bound by theory, it is believed that, in some embodiments, monohalide enrichment also proceeds via olefin formation followed by reaction with polyhalogenated alkanes. In some embodiments, reproportionation is facilitated by a catalyst.

The invention provides a number of unique subprocesses, improvements, and advantages, including reproportionation of polyhalides; recovery of halogen released during the requisite coke burn off; continuous regeneration of molecular halogen through the reaction of hydrogen halide and oxygen over a catalyst (allowing the overall process to operate continuously); and use of carefully selected anti-corrosion materials to address the inherently corrosive nature of the halogen-based process (allowing the process to be practiced commercially); and use of appropriate, reliable catalysts for long-term halogen generation. The bromination reactor can be operated adiabatically and over a wide temperature range. Carbon dioxide and water are easily tolerated, as are trace hydrocarbon impurities. Carbon loss due to coke formation is minimized by design by preferentially reacting monohalides over a coupling catalyst such as a zeolite or other reactive metal-oxygen material. Complete recovery of halogen for reuse is also an important advantage of the invention.

These discoveries, integrated into an overall process, are the basis for the invention and offer a true advance for such applications as the conversion of natural gas to liquid fuels (including gasoline and gasoline additives) and chemicals (including aromatics, such as benzene, xylene, and toluene, and light olefins, such as ethylene and propylene).

DETAILED DESCRIPTION

Figure 1:
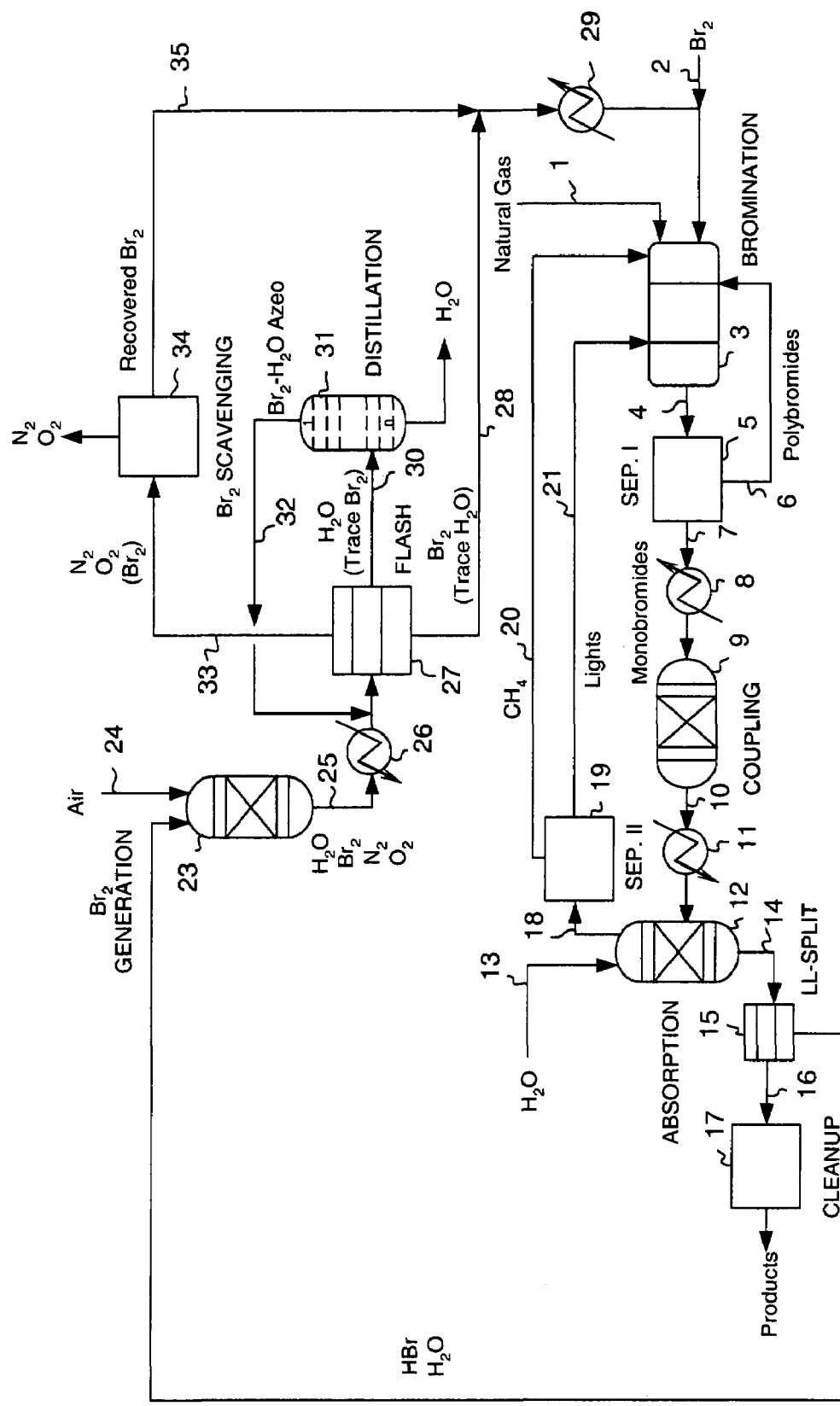
FIG. 1 is a schematic view of one embodiment of a continuous process for converting methane or natural gas into hydrocarbon chemicals according to the invention.

The present invention provides a chemical process that enables natural gas and other hydrocarbon feedstocks to be converted into higher molecular weight hydrocarbon products, using molecular halogen to activate C-H bonds in the feedstock. According to one aspect of the invention, a continuous process for converting a hydrocarbon feedstock into one or more higher hydrocarbons comprises the steps of (a) forming alkyl halides by reacting molecular halogen with a hydrocarbon feedstock (preferably a feedstock containing methane), under process conditions sufficient to form alkyl halides and hydrogen halide, whereby substantially all of the molecular halogen is consumed; (b) forming reproportionated alkyl halides by reacting some or all of the alkyl halides with an alkane feed, whereby the fraction of monohalogenated hydrocarbons present is increased; (c) contacting the reproportionated alkyl halides with a first catalyst under process conditions sufficient to form higher hydrocarbons and additional hydrogen halide; (d) separating the higher hydrocarbons from the hydrogen halide; (e) regenerating molecular halogen by contacting the hydrogen halide with a second catalyst in the presence of a source of oxygen, under process conditions sufficient to form molecular halogen and water; (f) separating the molecular halogen from water to allow reuse of the halogen; and (g) repeating steps (a) through (f) a desired number of times. These steps can be carried out in the order presented or, alternatively, in a different order.

According to a second aspect of the invention, a continuous process for converting a hydrocarbon feedstock into one or more higher hydrocarbons comprises the steps of (a) forming alkyl halides by reacting molecular halogen with a hydrocarbon feedstock containing methane in a halogenation reactor, under process conditions sufficient to form alkyl halides and hydrogen halide, whereby substantially all of the molecular halogen is consumed; (b) separating unreacted methane from the alkyl halides and directing it back into the halogenation reactor; (c) forming reproportionated alkyl halides by reacting some or all, of the alkyl halides with an alkane feed containing at least 1% by volume of one or more C2-C5 hydrocarbons, whereby the fraction of monohalogenated hydrocarbons present is increased; (d) contacting the reproportionated alkyl halides with a first catalyst under process conditions sufficient to form higher hydrocarbons and additional hydrogen halide; (e) separating the higher hydrocarbons from the hydrogen halide; (f) regenerating molecular halogen by contacting the hydrogen halide with a second catalyst in the presence of a source of oxygen, under process conditions sufficient to form molecular halogen and water; (g) separating the molecular halogen from water to allow reuse of the halogen; and (h) repeating steps (a) through (g) a desired number of times.

In each of the aspects and embodiments of the invention, it is intended that the alkyl halides formed in step (a) can be all the same (e.g., 100% bromomethane) or, more typically, different (e.g., mixtures of bromomethane, dibromomethane, dibromoethane, etc). Similarly, it is contemplated that the "higher hydrocarbons" formed in step (c) can be all the same (e.g., 100% isooctane) or, more typically, different (e.g., mixtures of aliphatic and/or aromatic compounds). As used herein, the term "higher hydrocarbons" refers to hydrocarbons having a greater number of carbon atoms than one or more components of the hydrocarbon feedstock, as well as olefinic hydrocarbons having the same or a greater number of carbon atoms as one or more components of the hydrocarbon feedstock. For instance, if the feedstock is natural gas— typically a mixture of light hydrocarbons, predominately methane, with lesser amounts of ethane, propane, and butane, and even smaller amounts of longer chain hydrocarbons such as pentane, hexane, etc.—the "higher hydrocarbon(s)" produced according to the invention can include a $C_2$ or higher hydrocarbon, such as ethane, propane, butane, $C_5$+ hydrocarbons, aromatic hydrocarbons, etc., and optionally ethylene, propylene, and/or longer olefins The term "light hydrocarbons" (sometimes abbreviated "LHCs") refers to $C_1$-$C_4$ hydrocarbons, e.g., methane, ethane, propane, ethylene, propylene, butanes, and butenes, all of which are normally gases at room temperature and atmospheric pressure.

Nonlimiting examples of hydrocarbon feedstocks appropriate for use in the present invention include alkanes, e.g., methane, ethane, propane, and even larger alkanes; olefins; natural gas and other mixtures of hydrocarbons. In most cases, the feedstock will be primarily aliphatic in nature. Certain oil refinery processes yield light hydrocarbon streams (so-called "light-ends," typically a mixture of $C_1$-$C_3$ hydrocarbons), which can be used with or without added methane as the hydrocarbon feedstock in one embodiment of the invention.

Representative halogens include bromine ($Br_2$) and chlorine ($Cl_2$). It is also contemplated that fluorine and iodine can be used, though not necessarily with equivalent results. Some of the problems associated with fluorine can likely be addressed by using dilute streams of fluorine (e.g., fluorine gas carried by helium, nitrogen, or other diluent). It is expected, however, that more vigorous reaction conditions will be required for alkyl fluorides to couple and form higher hydrocarbons, due to the strength of the fluorine-carbon bond. Similarly, problems associated with iodine (such as the endothermic nature of certain iodine reactions) can likely be addressed by carrying out the halogenation and/or coupling reactions at higher temperatures and/or pressures. The use of bromine or chlorine is preferred, with bromine being most preferred.

Figure 2:
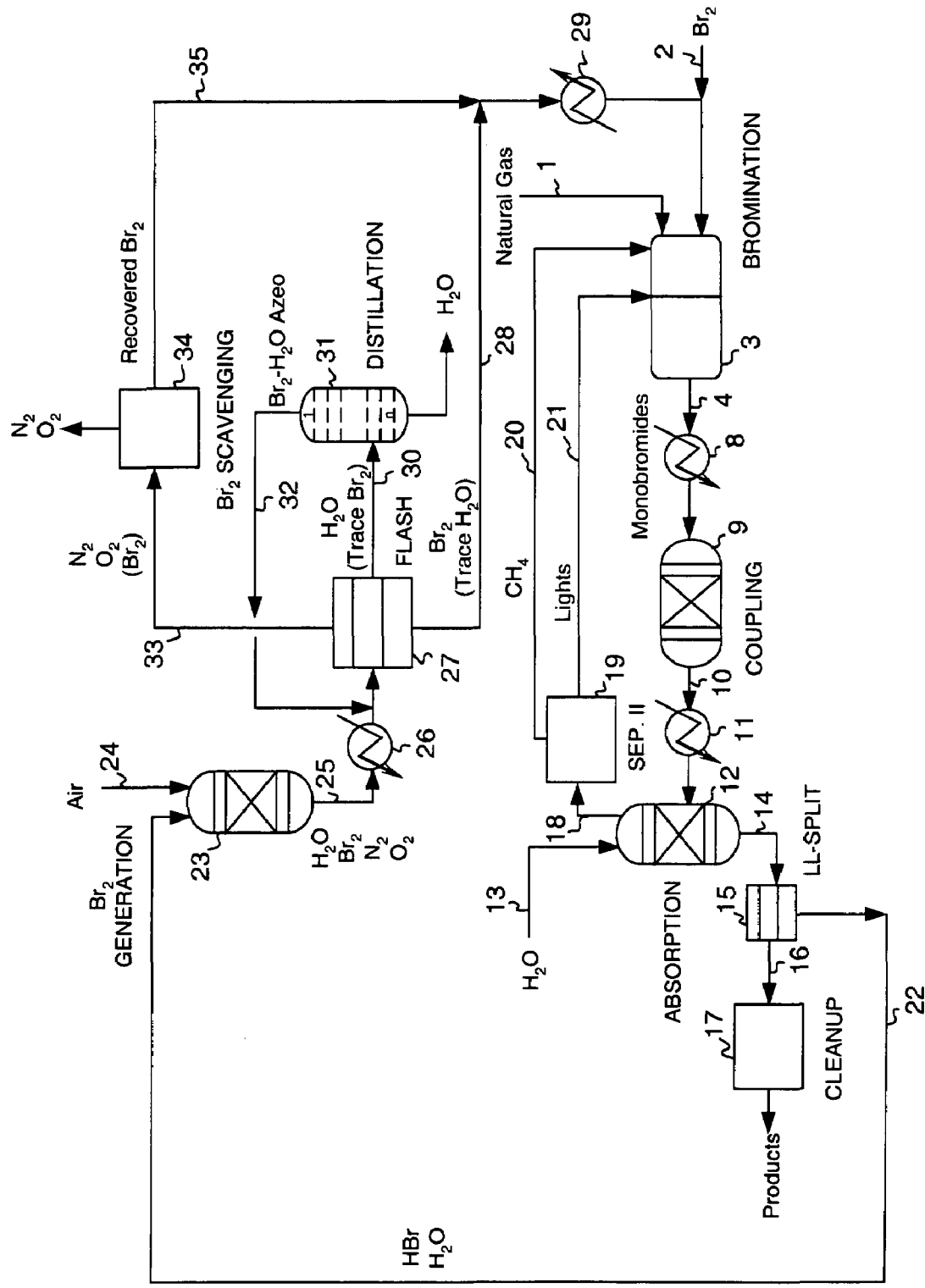
FIG. 2 is a schematic view of one embodiment of a continuous process for converting methane or natural gas into hydrocarbon fuels according to the invention.

FIGS. 1 and 2 schematically illustrate two nonlimiting embodiments of a process according to the invention, with FIG. 1 depicting a process for making hydrocarbon chemicals (e.g., benzene, toluene, xylenes, other aromatic compounds, etc.), and FIG. 2 depicting a process for making fuel-grade hydrocarbons, e.g., hydrocarbons comprising a predominant amount of $C_5$ and higher aliphatic hydrocarbons and (optionally) aromatic hydrocarbons. The primary difference in the two embodiments is that the process depicted in FIG. 2 lacks the first separation unit (SEP I) and does not return polybrominated species to the bromination reactor for "reproportionation." In the scheme shown in FIG. 2, the amount of polybromides produced is reduced significantly by introducing light gasses into the bromination reactor. The polybromides (from methane bromination) react with the light gasses to form monobromoalkanes. For convenience, the figures depict a bromine-based process. In alternate embodiments of the invention, however, chlorine or other halogens are used.

As shown in FIG. 1, natural gas (or another hydrocarbon feedstock) and molecular bromine are carried by separate lines 1, 2 into a heated bromination reactor 3 and allowed to react. Products (HBr, alkyl bromides, optionally olefins), and possibly unreacted hydrocarbons, exit the reactor and are carried by a line 4 into a first separation unit 5 (SEP I), where monobrominated hydrocarbons and HBr are separated from polybrominated hydrocarbons. The polybromides are carried by a line 6 back to the bromination reactor, where they undergo "reproportionation" with methane and/or other light hydrocarbons, which are present in the natural gas and/or introduced to the bromination reactor as described below.

Reproportionation of the polybromides formed during the bromination reaction enriches the outlet stream with monobromides and olefinic species, and reduces the amount of polybrominated hydrocarbons that enter the coupling reactor. This, in turn, reduces the amount of coke that forms during the carbon-carbon coupling reactions. For large scale production of aromatic hydrocarbons, it is possible to employ additional separation units, which can further purify the feed stream to the coupling reactor by separating and recycling the polybromides, thereby reducing the amount of coke and the overall bromine requirement.

Unreacted hydrocarbon feedstock, HBr, monobromides, and (optionally) olefins formed in the bromination reactor are carried by a line 7, through a heat exchanger 8, and enter a heated coupling reactor 9, where the monobromides (and, optionally, any olefins present) react in the presence of a coupling catalyst to form higher hydrocarbons. HBr, higher hydrocarbons, and (possibly) unreacted hydrocarbons and alkyl bromides exit the coupling reactor and are carried by a line 10, through another heat exchanger 11, and enter an HBr absorption unit 12. Water is introduced into the unit through a separate line 13. HBr is absorbed in this unit, which may be a packed column or other gas-liquid contacting device. The effluent, containing liquid hydrocarbons and aqueous HBr, is carried by a line 14 to a liquid-liquid splitter 15, which phase-separates liquid hydrocarbons from the aqueous HBr stream. The liquid hydrocarbon products are then carried by a line 16 to a product clean-up unit 17 to yield final hydrocarbon products.

After HBr is separated from the hydrocarbon products and unreacted methane (and any other light hydrocarbons that may be present) in the HBr absorption unit, the methane (and other light hydrocarbons, if any) is carried by a line 18 into a second separation unit 19 (SEP II), which employs pressure- or temperature-swing adsorption, membrane-based separation, cryogenic distillation (preferable for large scale production), or another suitable separation technology. Methane, and possibly other light hydrocarbons, are returned to the bromination reactor via one or more lines 20, 21. In the embodiment shown, methane is directed to an upstream region or "zone" of the bromination reactor, while other light hydrocarbons are directed to a mid- or downstream zone of the reactor (the latter to facilitate reproportionation of polybromides).

The aqueous HBr stream that evolves from the liquid-liquid splitter is carried by a line 22 to a bromine generation unit 23. Oxygen, air, or oxygen-enriched gas is also fed into the unit through a separate line 24. Bromine is regenerated by reacting HBr with oxygen in the presence of a suitable catalyst. The resulting stream contains water, molecular bromine, oxygen, nitrogen (if air was used as the source of oxygen), and possibly other gases. This product stream is carried by a line 25 through a heat exchanger 26 into a flash vaporization unit 27, which separates most of the molecular bromine from water, oxygen, nitrogen, and other gases (if any) that are present. Molecular bromine, either as a liquid or vapor (and containing no more than a trace of $H_2O$), is carried by a line 28 to a heat exchanger 29, and then returned to the bromination reactor.

Water from the flash vaporization unit (containing up to 3 wt % of molecular bromine) is sent by a line 30 to a distillation unit 31, which yields water as the bottoms stream and bromine or bromine-water azeotrope as a distillate The distillate is returned through a line 32 back to the flash vaporization unit.

The gaseous products of the flash vaporization unit (e.g., oxygen, nitrogen, optionally other gases, and no more than a minor or trace amount of bromine) are carried by a line 33 to a bromine scavenging unit 34, which separates molecular bromine from the other gases. The recovered bromine is then carried by a line 35 through a heat exchanger 29 and reintroduced into the bromination reactor. The amount of bromine entering the scavenger can be further reduced by increasing the amount of bromine recovered in the flash step by employing brine solutions and direct contact cooling to allow the use of temperatures below 0° Centigrade. The other gases (e.g., nitrogen, oxygen) can be vented to the atmosphere.

Various embodiments and features of individual subprocesses and other improvements for carrying out the invention will now be described in more detail.

Bromination

Bromination of the hydrocarbon feedstock is carried out in a fixed bed, fluidized bed, or other suitable reactor, at a temperature and pressure such that the bromination products and reactants are gases, for example, 1-50 atm, 150-600° C., more preferably 400-600° C., even more preferably, 450-515° C., with a residence time of 1-60 seconds, more preferably 1-15 seconds. Higher temperatures tend to favor coke formation, while low temperatures require larger reactors. Using a fluidized bed offers the advantage of improved heat transfer.

Alkane bromination can be initiated using heat or light, with thermal means being preferred. In one embodiment, the reactor also contains a halogenation catalyst, such as a zeolite, amorphous alumino-silicate, acidic zirconia, tungstates, solid phosphoric acids, metal oxides, mixed metal oxides, metal halides, mixed metal halides (the metal in such cases being, e.g., nickel, copper, cerium, cobalt, etc.), and/or or other catalysts as described, e.g., in U.S. Pat. Nos. 3,935,289 and 4,971,664. In an alternate embodiment, the reactor contains a porous or non-porous inert material that provides sufficient surface area to retain coke formed in the reactor and prevent it from escaping. The inert material may also promote the formation of polyhalogenated hydrocarbons, such as tribromopropane. In still another embodiment, both a catalyst and an inert material are provided in the reactor. Optionally, the reactor contains different regions or zones to allow, in or more zones, complete conversion of molecular bromine to produce alkyl bromides and hydrogen bromide.

The bromination reaction can also be carried out in the presence of an isomerization catalyst, such as a metal bromide (e.g., NaBr, KBr, CuBr, $NiBr_2$, $MgBr_2$, $CaBr_2$,), metal oxide (e.g., $SiO_2$, $ZrO_2$, $Al_2O_3$,), or metal (Pt, Pd, Ru, Ir, Rh) to help generate the desired brominated isomer(s). Since isomerization and bromination conditions are similar, the bromination and isomerization can be carried out in the same reactor vessel. Alternatively, a separate isomerization reactor can be utilized, located downstream of the bromination reactor and upstream of the coupling reactor.

Reproportionation

In some embodiments, a key feature of the invention is the "reproportionation" of polyhalogenated hydrocarbons (polyhalides), i.e., halogenated hydrocarbons containing two or more halogen atoms per molecule. Monohalogenated alkanes (monohalides) created during the halogenation reaction are desirable as predominant reactant species for subsequent coupling reactions and formation of higher molecular weight hydrocarbons. For certain product selectivities, polyhalogenated alkanes may be desirable. Reproportionation allows a desired enrichment of monohalides to be achieved by reacting polyhalogenated alkyl halides with nonhalogenated alkanes, generally in the substantial absence of molecular halogens, to control the ratio of mono-to-polyhalogenated species. For example, dibromomethane is reacted with methane to produce methyl bromide; dibromomethane is reacted with propane to produce methyl bromide and propyl bromide and/or propylene; and so forth.

Reactive reproportionation is accomplished by allowing the hydrocarbon feedstock and/or recycled alkanes to react with polyhalogenated species from the halogenation reactor, preferably in the substantial absence of molecular halogen. As a practical matter, substantially all of the molecular halogen entering the halogenation reactor is quickly consumed, forming mono- and polyhalides; therefore reproportionation of higher bromides can be accomplished simply by introducing polybromides into a mid- or downstream region or "zone" of the halogenation reactor, optionally heated to a temperature that differs from the temperature of the rest of the reactor.

Figure 3:
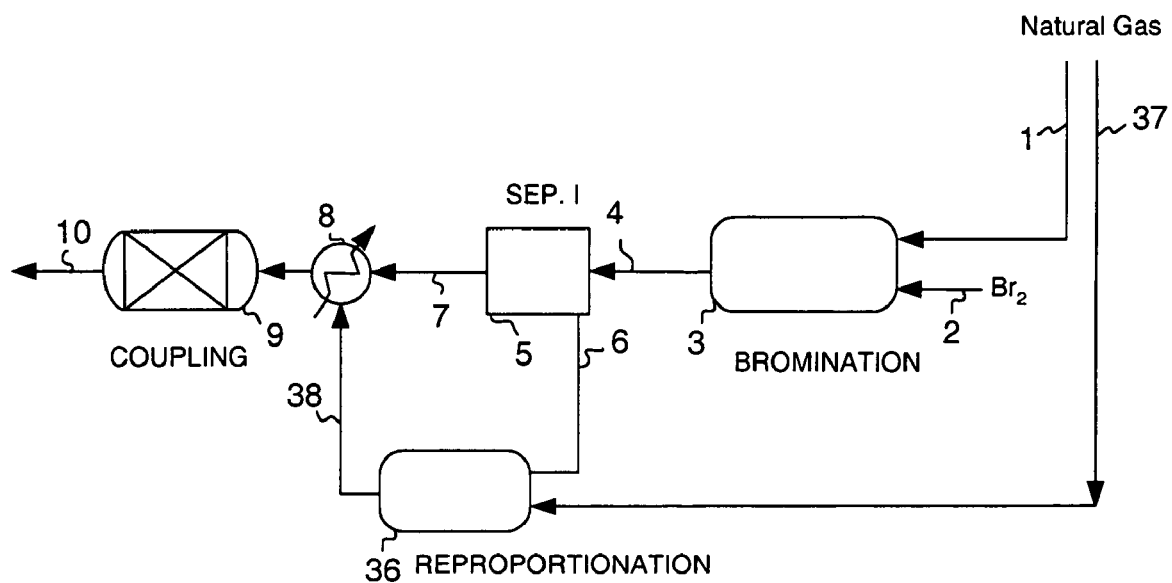
FIG. 3 is a schematic view of a subprocess for reproportionating polyhalides according to an alternate embodiment of the invention.

Alternatively, reproportionation can be carried out in a separate "reproportionation reactor," where polyhalides and unhalogenatated alkanes are allowed to react, preferably in the substantial absence of molecular halogen. FIG. 3 illustrates one such embodiment where, for clarity, only significant system elements are shown. As in FIG. 1, natural gas or another hydrocarbon feedstock and molecular bromine are carried by separate lines 1, 2 to a heated bromination reactor 3 and allowed to react. Products (HBr, alkyl bromides) and possibly unreacted hydrocarbons, exit the reactor and are carried by a line 4 into a first separation unit 5 (SEP I), where monobrominated hydrocarbons and HBr are separated from polybrominated hydrocarbons. The monobromides, HBr, and possibly unreacted hydrocarbons are carried by a line 7, through a heat exchanger 8, to a coupling reactor 9, and allowed to react, as shown in FIG. 1. The polybromides are carried by a line 6 to a reproportionation reactor 36. Additional natural gas or other alkane feedstock is also introduced into the reproportionation reactor, via a line 37. Polybromides react with unbrominated alkanes in the reproportionation reactor to form monobromides, which are carried by a line 38 to the coupling reactor 9, after first passing through a heat exchanger.

In another embodiment of the invention (not shown), where the hydrocarbon feedstock comprises natural gas containing a considerable amount of C2 and higher hydrocarbons, the "fresh" natural gas feed is introduced directly into the reproportionation reactor, and recycled methane (which passes through the reproportionation reactor unconverted) is carried back into the halogenation reactor.

Reproportionation is thermally driven and/or facilitated by use of a catalyst. Nonlimiting examples of suitable catalysts include metal oxides, metal halides, and zeolites. U.S. Pat. No. 4,654,449 discloses the reproportionation of polyhalogenated alkanes with alkanes using an acidic zeolite catalyst. U.S. Pat. Nos. 2,979,541 and 3,026,361 disclose the use of carbon tetrachloride as a chlorinating agent for methane, ethane, propane and their chlorinated analogues. All three patents are incorporated by reference herein in their entirety. Using reproportionation in the context of a continuous process for the enrichment of reactive feed stocks for the production of higher hydrocarbons has never been disclosed to our knowledge.

Reproportionation of C1-C5 alkanes with dibromomethane and/or other polybromides occurs at temperatures ranging from 350 to 550° C., with the optimal temperature depending on the polybromide(s) that are present and the alkane(s) being brominated. In addition, reproportionation proceeds more quickly at elevated pressures (e.g., 2-30 bar). By achieving a high initial methane conversion in the halogenation reactor, substantial amounts of di- and tribromomethane are created; those species can then be used as bromination reagents in the reproportionation step. Using di- and tribromomethane allows for controlled bromination of C1-C5 alkanes to monobrominated C1-C5 bromoalkanes and C2-C5 olefins. Reproportionation of di- and tribromomethane facilitates high initial methane conversion during bromination, which should reduce the methane recycle flow rate and enrich the reactant gas stream with C2-C5 monobromoalkanes and olefins, which couple to liquid products over a variety of catalysts, including zeolites. This is a major new process advance.

In another embodiment of the invention, reproportionation is carried out without first separating the polyhalides in a separation unit. This is facilitated by packing the "reproportionation zone" with a catalyst, such as a zeolite, that allows the reaction to occur at a reduced temperature. For example, although propane reacts with dibromomethane to form bromomethane and bromopropane (an example of "reproportionation"), the reaction does not occur to an appreciable degree at temperatures below about 500° C. The use of a zeolite may allow reproportionation to occur at a reduced temperature, enabling species such as methane and ethane to be brominated in one zone of the reactor, and di-, tri-, and other polybromides to be reproportionated in another zone of the reactor.

Bromine Recovery During Decoking

Inevitably, coke formation will occur in the halogenation and reproportionation processes. If catalysts are used in the reactor(s) or reactor zone(s), the catalysts may be deactivated by the coke; therefore, periodic removal of the carbonaceous deposits is required. In addition, we have discovered that, within the coke that is formed, bromine may also be found, and it is highly desirable that this bromine be recovered in order to minimize loss of bromine in the overall process, which is important for both economic and environmental reasons.

Several forms of bromides are present: HBr, organic bromides such as methyl bromide and dibromomethane, and molecular bromine. The invention provides means for recovering this bromine from the decoking process. In a preferred embodiment, a given reactor is switched off-line and air or oxygen is introduced to combust the carbon deposits and produce HBr from the residual bromine residues. The effluent gas is added to the air (or oxygen) reactant stream fed to the bromine generation reactor, thereby facilitating complete bromine recovery. This process is repeated periodically.

While a given reactor is off-line, the overall process can, nevertheless, be operated without interruption by using a reserve reactor, which is arranged in parallel with its counterpart reactor. For example, twin bromination reactors and twin coupling reactors can be utilized, with process gasses being diverted away from one, but not both, bromination reactors (or coupling reactors) when a decoking operation is desired. The use of a fluidized bed may reduce coke formation and facilitate the removal of heat and catalyst regeneration.

Another embodiment of the decoking process involves non-oxidative decoking using an alkane or mixture of alkanes, which may reduce both the loss of adsorbed products and the oxygen requirement of the process. In another embodiment of the decoking process, an oxidant such as oxygen, air, or enriched air is co-fed into the bromination section to convert the coke into carbon dioxide and/or carbon monoxide during the bromination reaction, thus eliminating or reducing the off-line decoking requirement.

Alkyl Halide Separation

The presence of large concentrations of polyhalogenated species in the feed to the coupling reactor can result in an increase in coke formation. In many applications, such as the production of aromatics and light olefins, it is desirable to feed only monohalides to the coupling reactor to improve the conversion to products. In one embodiment of the invention, a specific separation step is added between the halogenation/reproportionation reactor(s) and the coupling reactor.

For example, a distillation column and associated heat exchangers ("SEP I" in FIGS. 1 and 2) can be used to separate the monobromides from the polybrominated species by utilizing the large difference in boiling points of the compounds. The polybrominated species that are recovered as the bottoms stream can be reproportionated with alkanes to form monobromide species and olefins, either in the bromination reactor or in a separate reproportionation reactor. The distillation column can be operated at any pressure of from 1 to 50 bar. The higher pressures allow higher condenser temperatures to be used, thereby reducing the refrigeration requirement.

Figure 4:
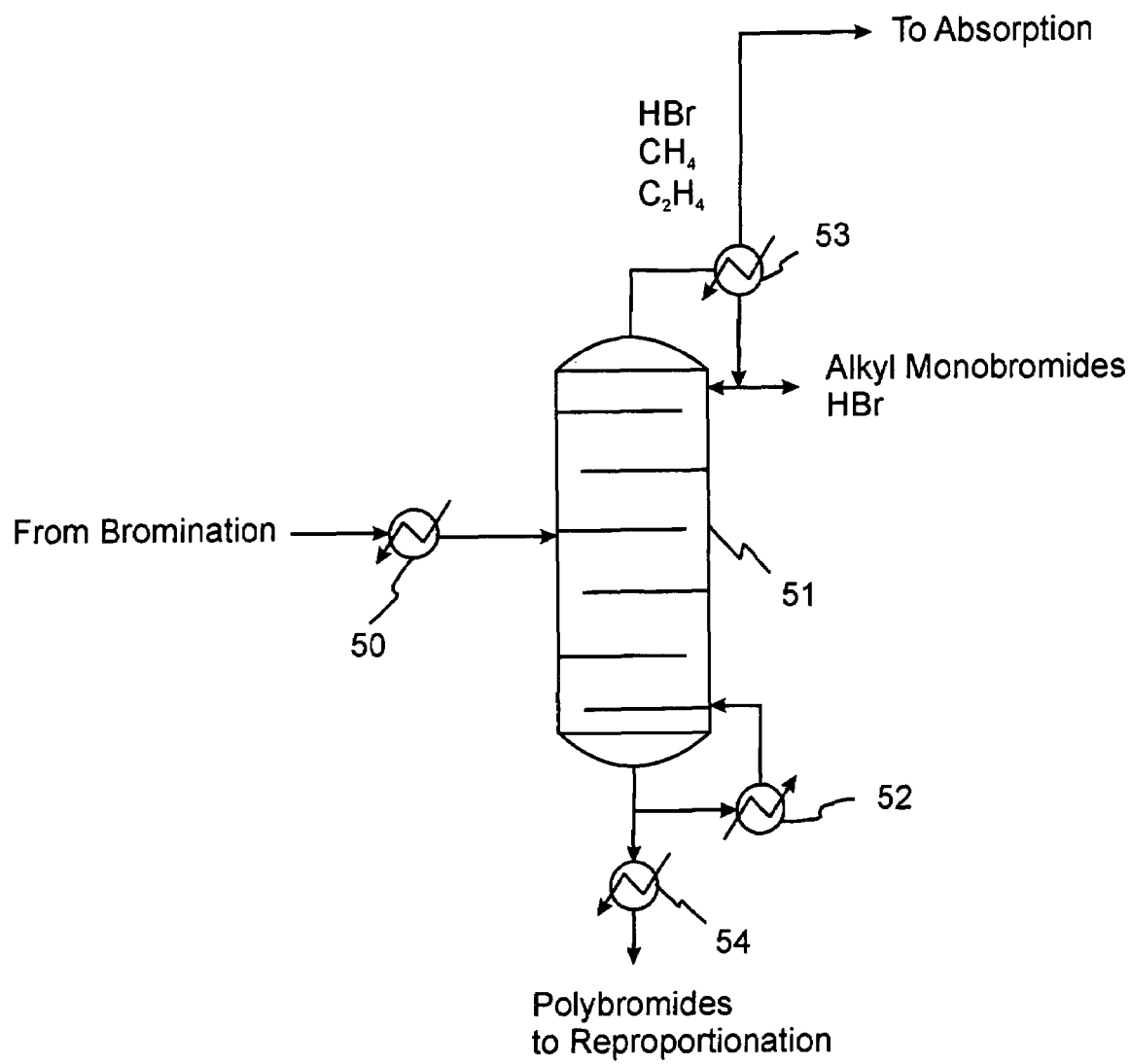
FIG. 4 is a schematic view of one embodiment of a monobromide separation column, for use in the practice of the invention.

FIG. 4 illustrates one embodiment of a separation unit for separating monobromides from polybrominated species. Alkyl bromides from the bromination reactor are cooled by passing through a heat exchanger 50, and then provided to a distillation column 51 equipped with two heat exchangers 52 and 53. At the bottom of the column, heat exchanger 52 acts as a reboiler, while at the top of the column heat exchanger 53 acts as a partial condenser. This configuration allows a liquid "bottoms" enriched in polybromides (and containing no more than a minor amount of monobromides) to be withdrawn from the distillation column. The polybromides are passed through another heat exchanger 54 to convert them back to a gas before they are returned to the bromination reactor (or sent to a separate reproportionation reactor) for reproportionation with unbrominated alkanes. At the top of the column, partial reflux of the liquid from the reflux drum is facilitated by the heat exchanger 53, yielding a vapor enriched in lighter components including methane and HBr, and a liquid stream comprised of monobromides and HBr (and containing no more than a minor amount of polybromides).

Alternate distillation configurations include a side stream column with and without a side stream rectifier or stripper. If the feed from the bromination reactor contains water, the bottoms stream from the distillation column will also contain water, and a liquid-liquid phase split on the bottoms stream can be used to separate water from the polybrominated species. Due to the presence of HBr in the water stream, it can either be sent to a HBr absorption column or to the bromine generation reactor.

Catalytic Coupling of Alkyl Halides to Higher Molecular Weight Products

The alkyl halides produced in the halogenation/reproportionation step are reacted over a catalyst to produce higher hydrocarbons and hydrogen halide. The reactant feed can also contain hydrogen halide and unhalogenated alkanes from the bromination reactor. According to the invention, any of a number of catalysts are used to facilitate the formation of higher hydrocarbon products from halogenated hydrocarbons. Nonlimiting examples include non-crystalline alumino silicates (amorphous solid acids), tungsten/zirconia super acids, sulfated zirconia, alumino phosphates such as SAPO-34 and its framework-substituted analogues (substituted with, e.g., Ni or Mn), Zeolites, such as ZSM-5 and its ion-exchanged analogs, and framework substituted ZSM-5 (substituted with Ti, Fe, Ti+Fe, B, or Ga). Preferred catalysts for producing liquid-at-room-temperature hydrocarbons include ion-exchanged ZSM-5 having a $SiO_2/Al_2O_3$ ratio below 300, preferably below 100, and most preferably 30 or below. Nonlimiting examples of preferred exchanged ions include ions of Ag, Ba, Bi, Ca, Fe, Li, Mg, Sr, K, Na, Rb, Mn, Co, Ni, Cu, Ru, Pb, Pd, Pt, and Ce. These ions can be exchanged as pure salts or as mixtures of salts. The preparation of doped zeolites and their use as carbon-carbon coupling catalysts is described in Patent Publication No. US 2005/0171393 A1, at pages 4-5, which is incorporated by reference herein in its entirety.

In one embodiment of the invention a Mn-exchanged ZSM-5 zeolite having a $SiO_2/Al_2O_3$ ratio of 30 is used as the coupling catalyst. Under certain process conditions, it can produce a tailored selectivity of liquid hydrocarbon products.

Coupling of haloalkanes preferably is carried out in a fixed bed, fluidized bed, or other suitable reactor, at a suitable temperature (e.g., 150-600° C., preferably 275-425° C.) and pressure (e.g., 0.1 to 35 atm) and a residence time ($\tau$) of from 1-45 seconds. In general, a relatively long residence time favors conversion of reactants to products, as well as product selectivity, while a short residence time means higher throughput and (possibly) improved economics. It is possible to direct product selectivity by changing the catalyst, altering the reaction temperature, and/or altering the residence time in the reactor. For example, at a moderate residence time of 10 seconds and a moderate temperature of 350° C., xylene and mesitylenes are the predominant components of the aromatic fraction (benzene+toluene+xylenes+mesitylenes; "BTXM") produced when the product of a methane bromination reaction is fed into a coupling reactor packed with a metal-ion-impregnated ZSM-5 catalyst, where the impregnation metal is Ag, Ba, Bi, Ca, Co, Cu, Fe, La, Li, Mg, Mn, Ni, Pb, Pd, or Sr, and the ZSM-5 catalyst is Zeolyst CBV 58, 2314, 3024, 5524, or 8014, (available from Zeolyst International (Valley Forge, Pa.)). At a reaction temperature of 425° C. and a residence time of 40 seconds, toluene and benzene are the predominant products of the BTXM fraction. Product selectivity can also be varied by controlling the concentration of dibromomethane produced or fed into the coupling reactor. Removal of reaction heat and continuous decoking and catalyst regeneration using a fluidized bed reactor configuration for the coupling reactor is anticipated in some facilities.

In one embodiment, the coupling reaction is carried out in a pair of coupling reactors, arranged in parallel. This allows the overall process to be run continuously, without interruption, even if one of the coupling reactors is taken off line for decoking or for some other reason. Similar redundancies can be utilized in the bromination, product separation, halogen generation, and other units used in the overall process.

Hydrocarbon Product Separation and Halogen Recovery

The coupling products include higher hydrocarbons and HBr. In the embodiments shown in FIGS. 1 and 2, products that exit the coupling reactor are first cooled in a heat exchanger and then sent to an absorption column. HBr is absorbed in water using a packed column or other contacting device. Input water and the product stream can be contacted either in a co-current or counter-current flow, with the counter-current flow preferred for its improved efficiency. HBr absorption can be carried out either substantially adiabatically or substantially isothermally. In one embodiment, the concentration of hydrobromic acid after absorption ranges from 5 to 70 wt %, with a preferred range of 20 to 50 wt %. The operating pressure is 1 to 50 bar, more preferably 1 to 30 bar. In the laboratory, a glass column or glass-lined column with ceramic or glass packing can be used. In a pilot or commercial plant, one or more durable, corrosion-resistant materials (described below) are utilized.

In one embodiment of the invention, the hydrocarbon products are recovered as a liquid from the HBr absorption column. This liquid hydrocarbon stream is phase-separated from the aqueous HBr stream using a liquid-liquid splitter and sent to the product cleanup unit. In another embodiment, the hydrocarbon products are recovered from the HBr column as a gas stream, together with the unconverted methane and other light gases. The products are then separated and recovered from the methane and light gases using any of a number of techniques. Nonlimiting examples include distillation, pressure swing adsorption, and membrane separation technologies.

In some embodiments, the product clean-up unit comprises or includes a reactor for converting halogenated hydrocarbons present in the product stream into unhalogenated hydrocarbons. For example, under certain conditions, small amounts of C1-C4 bromoalkanes, bromobenzene, and/or other brominated species are formed and pass from the coupling reactor to the liquid-liquid splitter 16 and then to the product clean-up unit 17. These brominated species can be "hydrodehalogenated" in a suitable reactor. In one embodiment, such a reactor comprises a continuous fixed bed, catalytic converter packed with a supported metal or metal oxide catalyst, Nonlimiting examples of the active component include copper, copper oxide, palladium, and platinum, with palladium being preferred. Nonlimiting examples of support materials include active carbon, alumina, silica, and zeolites, with alumina being preferred. The reactor is operated at a pressure of 0-150 psi, preferably 0-5 psi, and a temperature of 250-400° C., preferably 300-350° C., with a GHSV of 1200-60 $hr^{-1}$, preferably ~240 $hr^{-1}$. When bromobenzene (e.g.) is passed over such a reactor, it is readily converted to benzene and HBr, with some light hydrocarbons (e.g., C3-C7) produced as byproducts. Although carbon deposition (coking) can deactivate the catalyst, the catalyst can be regenerated by exposure to oxygen and then hydrogen at, e.g., 500° C. and 400° C., respectively.

After HBr is separated from the hydrocarbon products, the unconverted methane leaves with the light gases in the vapor outlet of the HBr absorption unit. In one embodiment of the invention, unconverted methane is separated from the light gases in a separation unit ("SEP II" in the FIGS.), which operates using pressure or temperature swing adsorption, membrane-based separation, cryogenic distillation (preferable for large-scale production), or some other suitable separation process. Low methane conversions in the bromination reactor may result in the coupling products being carried with the light gases, which in turn would necessitate the recovery of these species from the lights gases. Separation technologies that can be employed for this purpose include, but are not limited to, distillation, pressure or temperature swing adsorption, and membrane-based technologies.

Figure 5:
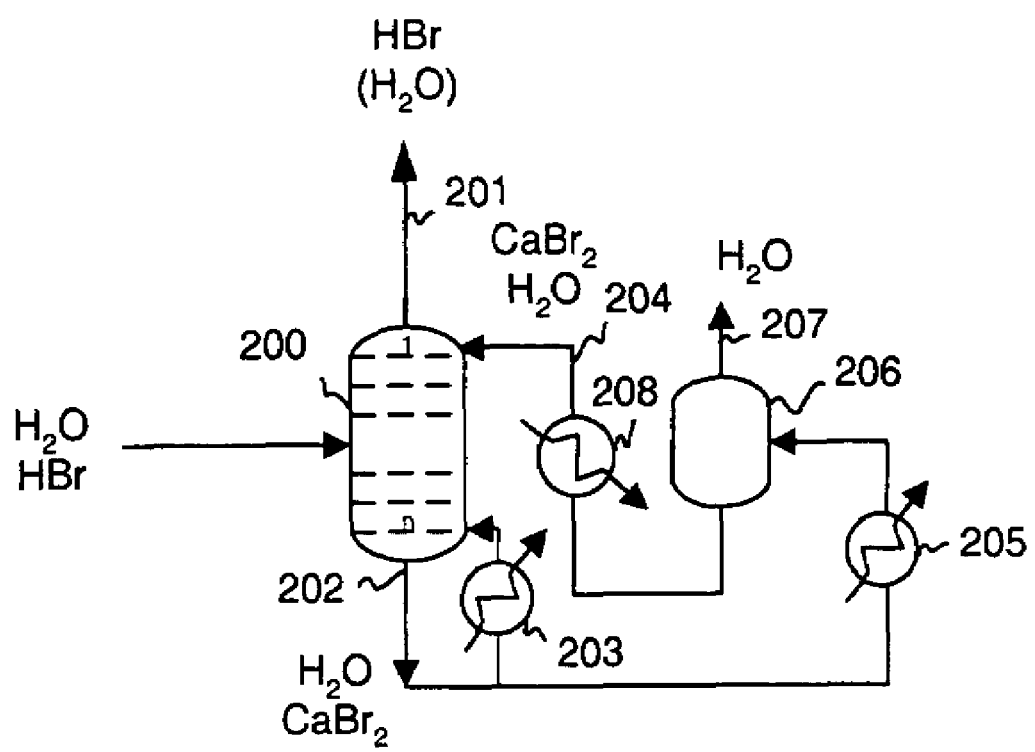
FIG. 5 is a schematic view of one embodiment of an extractive distillation system, for use in the practice of the invention

In another aspect of the invention, a process for separating anhydrous HBr from an aqueous solution of HBr is provided. HBr forms a high-boiling azeotrope with water; therefore, separation of HBr from the aqueous solution requires either breaking the azeotrope using an extractive agent or bypassing the azeotrope using pressure swing distillation. FIG. 5 illustrates one embodiment of an extractive distillation unit for separating HBr from water. Water is extracted in a distillation column 200 and HBr is obtained as the distillate stream 201. The distillate stream may also contain small amounts of water. In one embodiment, the distillation column 200 is a tray-tower or a packed column. Conventional ceramic packing is preferred over structured packing. Aqueous bromide sale, such as $CaBr_2$, is added at the top of the distillation column, resulting in the extraction of water from aqueous HBr. A condenser may not be required for the column. A reboiler 203 is used to maintain the vapor flow in the distillation column. The diluted stream of aqueous $CaBr_2$ 202 is sent to the evaporation section 206, which, optionally has a trayed or packed section. The bottoms stream from the column is heated before entering the evaporation section. Stream 207 comprising mostly water (and no more than traces of HBr) leaves the evaporation section.

In one embodiment, HBr is displaced as a gas from its aqueous solution in the presence of an electrolyte that shares a common ion ($Br^{31}$ or $H^+$) or an ion (e.g. $Ca^{2+}$ or $SO_4^{2-}$) that has a higher hydration energy than HBr. The presence of the electrolyte pushes the equilibrium $HBr_{aq} \leftarrow \rightarrow HBr_{gas}$ towards gas evolution, which is further facilitated by heating the solution.

Aqueous solutions of metal bromides such as $CaBr_2$, $MgBr_2$ also KBr, NaBr, LiBr, RbBr, CsBr, $SrBr_2$, $BaBr_2$, $MnBr_2$, $FeBr_2$, $FeBr_3$, $CoBr_2$, $NiBr_2$, $CuBr_2$, $ZnBr_2$, $CdBr_2$, $AlBr_3$, $LaBr_3$, $YBr_3$, and $BiBr_3$ can be used as extractive agents, with aqueous solutions of $CaBr_2$, $MgBr_2$, KBr, NaBr, LiBr or mixtures thereof being preferred. The bottoms stream of the distillation column contains a diluted solution of the extracting agent. This stream is sent to another distillation column or a vaporizer where water is evaporated and the extracting agent is concentrated before sending it back to the extractive distillation column. Sulfuric acid can be used as an extracting agent if its reaction with HBr to form bromine and sulfur dioxide can be minimized. Experiments carried out to demonstrate the separation of anhydrous HBr from an aqueous solution of HBr are described in Example 1 and 2.

In another aspect of the invention, various approaches to product clean-up (separation and/or purification) are provided. A number of bromide species may be present in the unpurified product stream: HBr, organic bromides such as methyl bromide and dibromomethane, and bromo-aromatics. In one embodiment of the invention, hydrocarbon products are separated from brominated species by passing the product stream over copper metal, NiO, CaO, ZnO, MgO, BaO, or combinations thereof. Preferably, the products are run over one or more of the above-listed materials at a temperature of from 25-600° C., more preferably, 400-500° C. This process is tolerant of $CO_2$ that may be present.

In another embodiment, particularly for large-scale production of hydrocarbons, unconverted methane is separated from other light hydrocarbons as well as heavier products (e.g., benzene, toluene, etc.) using distillation. For example, in FIGS. 1 and 2, methane and other light hydrocarbons exit the absorption column through a gas outlet and are directed to a separation unit (SEP. II). Any unconverted methyl bromide will be removed with the light gases and can be recycled back to the bromination/reproportionation reactor. Heavier hydrocarbons are removed as a liquid distillate.

Molecular Halogen Generation

In one embodiment of the invention, catalytic halogen generation is carried out by reacting hydrohalic acid and molecular oxygen over a suitable catalyst. The general reaction can be represented by equation (1):

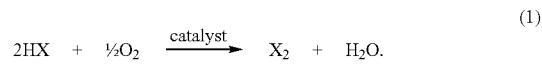

(1)

The process occurs at a range of temperatures and mole ratios of hydrohalic acid (HX) and molecular oxygen ($O_2$), i.e., 4:1 to 0.001:1 $HX/O_2$, preferably 4:1 (to fit the reaction stoichiometry), more preferably 3.5:1 (to prevent eventual HBr breakthrough).

Halogen can be generated using pure oxygen, air, or oxygen-enriched gas, and the reaction can be run with a variety of inert nonreacting gases such as nitrogen, carbon dioxide, argon, helium, and water steam being present. Any proportion of these gases can be combined as pure gases or selected mixtures thereof, to accommodate process requirements.

A number of materials have been identified as halogen generation catalysts. It is possible to use one type of catalyst or a combination of any number, configuration, or proportion of catalysts. Oxides, halides, and/or oxy-halides of one or more metals, such as Cu, Ag, Au, Fe, Co, Ni, Mn, Ce, V, Nb, Mo, Pd, Ta, or W are representative, more preferably Mg, Ca, Sr, Ba, V, Cr, Mn, Fe, Co, Ni, Cu, Zn, or Ce. The most preferable catalysts are oxides, halides, and/or oxy-halides of Cu.

Although not bound by theory, the following equations are considered representative of the chemistry believed to take place when such materials are used to catalyze halogen formation:

(2)

(3)

for metal oxides in which the metal does not change oxidation states, and

(4)

(5)

for metal oxides in which the metal does change oxidation states. The net reaction for (2)+(3) and (4)+(5) is (7):

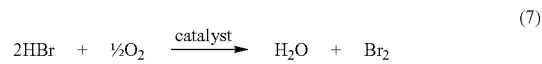

(7)

which is equivalent to (1).

In one embodiment of the invention, chlorine is used as the halogenating agent, and ceria ($CeO_2$) is used to catalyze the generation of chlorine from hydrochloric acid. The following equations are considered representative:

$$CeO_2 + 4HCl \rightarrow CeCl_2 + 2H_2O + Cl_2 \quad (8)$$

$$CeCl_2 + O_2 \rightarrow CeO_2 + Cl_2 \quad (9)$$

for an overall reaction:

$$2HCl + \tfrac{1}{2}O_2 \rightarrow H_2O + Cl_2 \quad (10)$$

which is also equivalent to (1).

This use of ceria is quite novel, as it allows essentially complete consumption of HCl. In contrast, previous reactions of metal oxides, HCl, and oxygen have typically yielded $HCl/Cl_2$ mixtures. Thus, ceria can advantageously be employed as a halogen regeneration catalyst, particularly where chlorine is used for alkane halogenation, with chlorine's attendant lower cost and familiarity to industry.

In one embodiment of the invention, the halogen generation catalyst(s) are supported on porous or nonporous alumina, silica, zirconia, titania or mixtures thereof, or another suitable support. A range of temperatures can be employed to maximize process efficiency, e.g., 200-600° C., more preferably 350-450° C.

Recovery and Recycle of Molecular Halogen

Halogen generation produces both water and molecular halogen. Water can be separated from halogen and removed before the halogen is reacted with the hydrocarbon feedstock. Where the halogen is bromine, a bromine-water, liquid-liquid phase split is achieved upon condensation of a mixture of these species. For example, in one embodiment of the invention, a liquid-liquid flash unit is used to separate most of the bromine from water, simply and inexpensively. The bromine phase typically contains a very small amount of water, and can be sent directly to the bromination reactor. The water phase, however, contains 1-3 wt % bromine. However, if air is used in the bromine generation step, nitrogen and unconverted oxygen are present with the bromine and water stream that enters the flash.

The gas leaving the flash unit primarily consists of nitrogen and unconverted oxygen, but carries with it some bromine and water. The amount of bromine leaving with the vapor phase depends on the temperature and pressure of the flash. The flash can be operated at temperatures ranging from 0 to 50° C.; however, a lower temperature (ca 2 to 10° C.) is preferred to reduce bromine leaving in the vapor stream. The vapor stream is sent to the bromine scavenging section for bromine recovery. In one embodiment, the operating pressure is 1 to 50 bar, more preferably 1 to 30 bar. Since water freezes at 0° C., it is not possible to substantially reduce the temperature of the flash 19. However, the vapor stream from the flash can be contacted with a chilled brine solution, at temperatures from −30° C. to 10° C. Chilled brine temperatures lower than that of the flash can substantially reduce the bromine scavenging requirement of the scavenging unit. Vaporizing the bromine by heating the brine can then occur, with further heating employed to facilitate concentration of the brine for re-use. This approach to bromine recovery can be carried out either continuously or in batch mode.

Bromine contained in the water-rich phase leaving the liquid-liquid flash can be effectively recovered by distillation. Other means, such as using an inert gas to strip the bromine from the water phase (described by Waycuilis) and adsorption-based methods, are not very effective, and potentially can result in a significant loss of bromine. The presently described distillation subprocess produces bromine or bromine-water azeotrope as a distillate, which is recycled back to the flash unit. Water is contained in the bottoms stream. Bromine can react reversibly with water to form small amounts of HBr and HOBr. In the distillation scheme, therefore, ppm levels of HBr (and/or HOBr) can be present in the bottoms stream. A side-stream rectifier or stripper can be utilized to reduce the bromine content of the bottoms stream to produce a pure water stream. Other alternatives that can reduce the bromine content of the water to below 10 ppm range include, but are not limited to, the addition of acids such as sulfuric acid, hydrochloric acid, and phosphoric acid, in very small quantities to reduce the pH of the water stream. Lowering the pH drives the HBr and HOBr stream back to bromine and water, thereby substantially reducing the loss of bromine in the water stream. HBr present in the water stream can also be recovered using ion-exchange resins or electrochemical means.

Recovery of all halogen for reuse. For both economic and environmental reasons, it is preferred to minimize, if not completely eliminate, loss of halogen utilized in the overall process. Molecular bromine has the potential to leave with vented nitrogen and unconverted oxygen if it is not captured after $Br_2$ generation. Bromine scavenging can be carried out in a bed containing solid CuBr or $MnBr_2$, either loaded on a support or used in powder form, to capture $Br_2$ from a gas stream that may also contain $H_2O$, $CO_2$, $O_2$, methane &/or $N_2$. In one embodiment of the invention, bromine scavenging is performed within a range of temperatures, i.e., from −10° to 200° C. When bromine scavenging is complete, molecular bromine can be released from the bed by raising the temperature of the bed to 220° C. or higher, preferably above 275° C. It is important that there be little if any $O_2$ in the bed during bromine release, as $O_2$ will oxidize the metal and, over time, reduce the bromine-scavenging capacity of the bed.

Construction of Critical Process Elements with Unique Corrosion-Resistant Materials Corrosion induced by any halogen-containing process, whether in the condensed phase or the vapor phase, presents a significant challenge in the selection of durable materials for the construction of reactors, piping, and ancillary equipment. Ceramics, such as alumina, zirconia, and silicon carbides, offer exceptional corrosion resistance to most conditions encountered in the process described herein. However, ceramics suffer from a number of disadvantages, including lack of structural strength under tensile strain, difficulty in completely containing gas phase reactions (due to diffusion or mass transport along jointing surfaces), and possibly undesirable thermal transport characteristics inherent to most ceramic materials. Constructing durable, gas-tight, and corrosion resistant process control equipment (i.e. shell and tube type heat-exchangers, valves, pumps, etc.), for operation at elevated temperatures and pressures, and over extended periods of time, will likely require the use of formable metals such as Au, Co, Cr, Fe, Nb, Ni, Pt, Ta, Ti, and/or Zr, or alloys of these base metals containing elements such as Al, B, C, Co, Cr, Cu, Fe, H, Ha, La, Mn, Mo, N, Nb, Ni, 0, P, Pd, S, Si, Sn, Ta, Ti, V, W, Y, and/or Zr.

According to one embodiment of the invention, the process and subprocesses described herein are carried out in reactors, piping, and ancillary equipment that are both strong enough and sufficiently corrosion-resistant to allow long-term continued operation. Selection of appropriate materials of construction depends strongly on the temperature and environment of exposure for each process control component.

Suitable materials for components exposed to cyclic conditions (e.g. oxidizing and reducing), as compared to single conditions (oxidizing or reducing), will differ greatly. Non-limiting examples of materials identified as suitable for exposure to cyclic conditions, operating in the temperature range of from 150-550° C., include Au and alloys of Ti and Ni, with the most suitable being Al/V alloyed Ti (more specifically Ti Grd-5) and Ni—Cr—Mo alloys with high Cr, low Fe, and low C content (more specifically ALLCOR®, Alloy 59, C-22, 625, and HX). Nonlimiting examples of materials identified as suitable for exposure to either acid halide to air, or molecular halogen to air cyclic conditions, in the temperature range 150-550° C., either acid halide to air, or molecular halogen to air include alloys of Fe and Ni, with the most suitable being alloys of the Ni—Cr—Mo, and Ni—Mo families. Nonlimiting examples of materials identified as suitable for single environment conditions, in the temperature range 100° C.-550° C., include Ta, Au, and alloys of Fe, Co, and Ni. For lower temperature conditions (<280° C.), suitable polymer linings can be utilized such as PTFE, FEP, and more suitably PVDF. All materials may be used independently or in conjunction with a support material such as coating, cladding, or chemical/physical deposition on a suitable low-cost material such as low-alloy steels.

Figure 6:
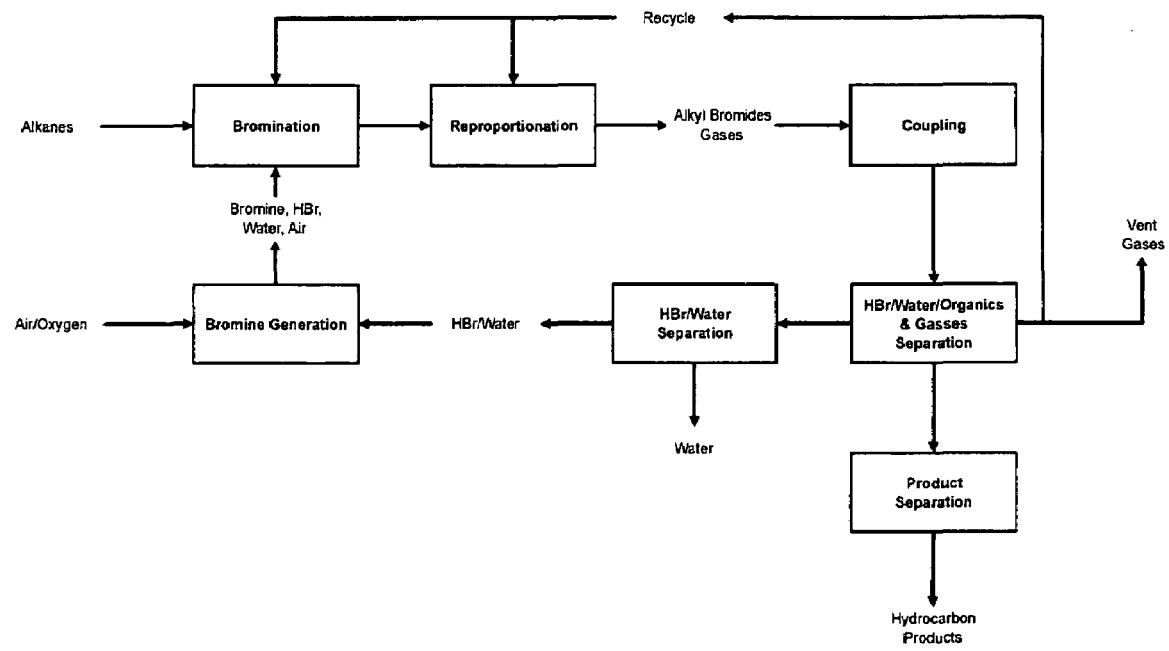
FIG. 6 is a simplified block diagram of one embodiment of a continuous process for converting alkanes into hydrocarbon products according to the invention, wherein water is separated from hydrocarbon products.

FIG. 6 schematically illustrates an alternate mode of operation for a continuous process for converting methane, natural gas, or other alkane feedstocks into higher hydrocarbons. Alkanes are brominated in the bromination section in the presence of water formed during bromine generation, including recycled water. The bromination products pass either through a reproportionation reactor or through the reproportionation section of the bromination reactor, where the light gases are reproportionated to form olefins and alkyl bromides by using the polybromides as brominating agents. The reproportionation products, which include olefins, alkyl monobromides, some polybromides, and HBr, along with any unreacted alkanes, are then sent to the coupling reactor. The coupling products are sent to a vapor-liquid-liquid flash. Higher hydrocarbon products are removed as an organic phase from the vapor-liquid-liquid flash, while aqueous HBr is removed as the heavier phase. The gas stream from the flash is sent to a separation system to recover methane and light gases, which are recycled back to the bromination and reproportionation sections, respectively.

Nitrogen must be removed from the gas recycle stream if air is used as an oxidant in bromine generation. The aqueous HBr stream coming out of the vapor-liquid-liquid flash is sent to the HBr/water separation system, where water is recovered. The separation can be carried out in a distillation column, where pure water is taken out as a distillate and the bottoms stream is an aqueous solution of HBr (having a higher concentration of HBr than the feed to the distillation column). The aqueous HBr stream is sent back to the bromine generation section, where bromine is generated from aqueous HBr in the presence of air or oxygen.

Alternatively, extractive distillation is used to separate HBr from water. The separated HBr is sent to the bromine generation reactor and bromine is generated from aqueous HBr in the presence of air or oxygen. Complete conversion of HBr is not necessary in the bromine generation reactor. Periodic decoking can be carried out for the bromination, reproportionation, and/or coupling reactors, with the bromine-containing decoking product stream being routed to the bromine generation reactor.

Figure 7:
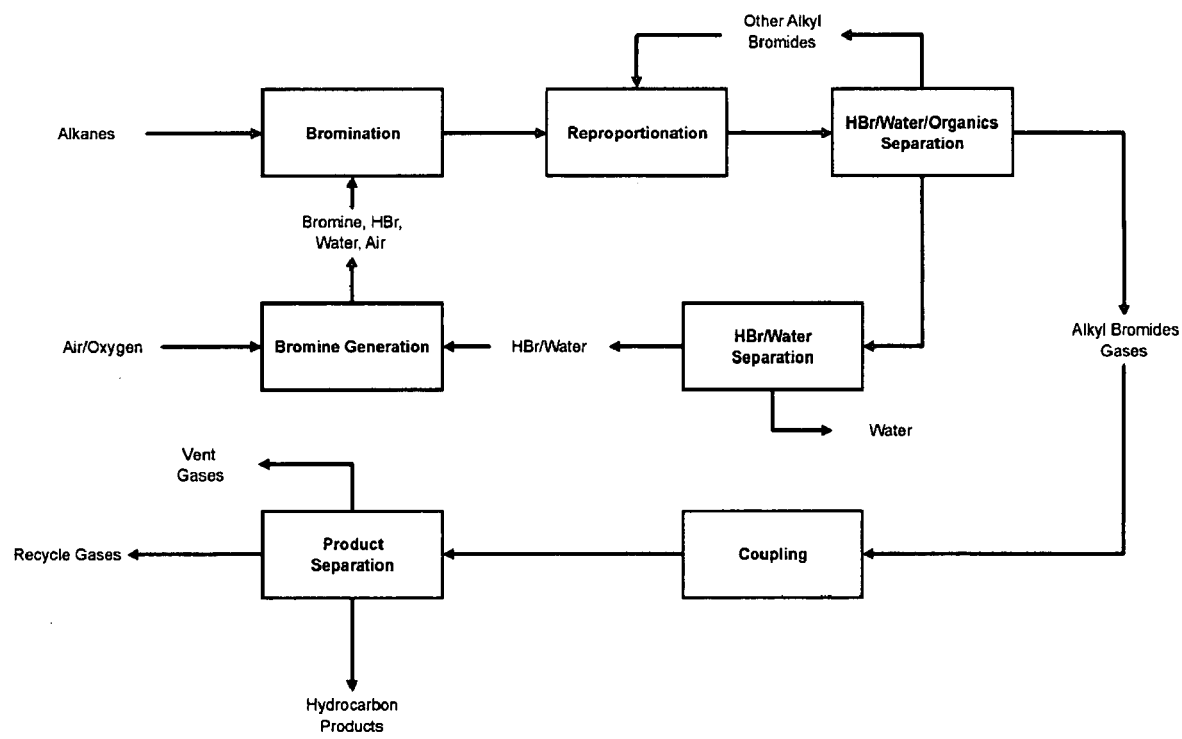
FIG. 7 is a simplified block diagram of one embodiment of a continuous process for converting alkanes into hydrocarbon products according to the invention, wherein water is separated after the alkane bromination step.

Another continuous process alternative is shown in FIG. 7. Alkanes are brominated in the bromination section in the presence of water formed during bromine generation, including recycled water. The bromination products (which include monobromides and polybromides) pass through either a reproportionation reactor or the reproportionation section of the bromination reactor, where the light gases are reproportionated to form alkyl bromides, using the polybromides as brominating agents. The reproportionation products—alkyl monobromides, olefins, a small amount of polybromides, and HBr—and any unreacted alkanes are then sent to a separation unit where aqueous HBr is separated from the alkyl bromides. Monobromides in the alkyl bromide stream are separated from the polybromides. The polybromides are recycled to the reproportionation section where polybromides react with the recycle gases to form olefins and monobromides.

The aqueous HBr separation from the alkyl bromides can be carried out in a distillation column coupled with a liquid-liquid flash. The alkyl bromide stream can contain HBr. The monobromides are fed into the coupling section, and the products are sent to a water absorption column where HBr produced in the coupling reactor is removed from the products and unconverted gas. The liquid outlet of the absorption column is fed to a vapor-liquid-liquid flash separation unit, where higher hydrocarbon products are removed as an organic phase and aqueous HBr is removed as the heavier phase. The gas outlet from the absorption column is sent to a separation system to separate methane from the light gases. The recovered methane is recycled back to the bromination section, while the light gases are recycled to the reproportionation section.

Nitrogen must be separated before the gases are recycled if air is used as an oxidant in bromine generation. The aqueous HBr stream from the vapor-liquid-liquid flash is combined with the aqueous HBr stream from the alkyl bromide separation section and sent to the HBr/Water separation system. The separation can be carried out in a distillation column, where pure water is taken out as a distillate and the bottoms stream is an aqueous solution of HBr having a higher concentration of HBr compared with the feed to the distillation column. The aqueous HBr stream is sent back to the bromine generation section, where bromine is generated from aqueous HBr in the presence of air, oxygen or enriched air.

Alternatively, extractive distillation is used to separate HBr from water. The separated HBr is sent to the bromine generation reactor, where bromine is generated from aqueous HBr in the presence of air, oxygen, or enriched air. Complete conversion of HBr to bromine is not required during bromine generation. Periodic decoking of the bromination, reproportionation and coupling reactors can be carried out, with the bromine-containing decoking product stream being routed to the bromine generation reactor.

The following are nonlimiting examples of the invention and various subprocesses for practicing the invention.

EXAMPLE 1

Reproportionation of Dibromomethane with Propane

Methane (11 sccm, 1 atm) was combined with nitrogen (15 sccm, 1 atm) at room temperature via a mixing tee and passed through a room temperature bubbler full of bromine. The $CH_4/N_2/Br_2$ mixture was plumbed into a preheated glass tube at 500° C., and bromination of the methane took place with a residence time ("$t_{res}$") of 60 seconds, producing primarily bromomethane, dibromomethane, and HBr. The stream of nitrogen, HBr, and partially brominated hydrocarbon was combined with propane (0.75 sccm, 1 atm) in a mixing tee and passed into a second glass reactor tube at 525° C. with a residence time ("$t_{res}$") of 60 s. In the second reactor tube, polybrominated hydrocarbons (i.e. $CH_2Br_2$, $CHBr_3$) react with the propane to produce bromopropanes. The reproportionation is idealized by the following reaction:

$$CH_2Br_2 + C_3H_8 \rightarrow CH_3Br + C_3H_7Br$$

As products left the second reactor, they were collected by a series of traps containing 4 M NaOH (which neutralized the HBr) and hexadecane (containing octadecane as an internal standard) to dissolve as much of the hydrocarbon products as possible. Volatile components like methane and propane were collected in a gas bag after the HBr/hydrocarbon traps. All products were quantified by gas chromatography. The results ("Ex. 1") are summarized in Table 1. For comparison, the reactions were also run with two reactors, but without reproportionation with propane ("Control A"), and with only the first reactor and without propane ("Control B").

TABLE 1

Reproportionation of Dibromomethane

|  | Ex. 1 (bromination/ reproportion- ation) | Control A (bromination) | Control B (bromination) |
|---|---|---|---|
| Bromination $t_{res}$ | 60 | 60 | 60 |
| Reproportionation $t_{res}$ | 60 | 60 | 0 |
| $CH_4$ conversion | 40% | 47% | 45% |
| $CH_3Br/(CH_3Br + CH_2Br_2)$ | 93% | 84% | 74% |
| $C_3H_8$ conversion | 85% | N/A | N/A |
| Carbon balance | 96% | 97% | 96% |

EXAMPLE 2

Separation of Anhydrous HBr 20 ml stock HBr aqueous solution were added to 20 g $CaBr_2 \cdot H_2O$ followed by heating to 70° C. A significant evolution of HBr gas was observed (determined by $AgNO_3$ precipitation and the $NH_3$ fuming test). The released HBr was not quantified as the reaction was carried out in an open vessel.

EXAMPLE 3

Separation of Anhydrous HBr

Dehydration with $H_2SO_4$ was attempted by adding a conc. solution of $H_2SO_4$ to HBr. Qualitative tests were conducted in which different concentration of $H_2SO_4$ were added to HBr for determination of the threshold concentration where oxidation of HBr no longer occurs:

$$2HBr + H_2SO_4 \rightarrow Br_2 + SO_2 + 2H_2O.$$

It was determined that the $H_2SO_4$ concentration below which no oxidation is apparent is ~70 wt. %. 30 ml 70% $H_2SO_4$ was added to 30 ml stock HBr azeotrope (48 wt. %) and the mixture was heated to boiling. The HBr content was determined quantitatively by $AgNO_3$ precipitation and gravimetric determination of AgBr from a solution aliquot at the moment of mixing, after 15 min and after 30 min. boiling.

EXAMPLE 4

Metathesis of Brominated Methane over Selected Catalysts

A series of experiments were conducted in which methane was brominated in a manner substantially the same as or similar to that described in Example 1 (10 sccm methane bubbled through room temperature bromine, followed by passage of the mixture through a reactor tube heated to 500° C.), and the bromination products were then passed over various metal-ion exchanged or impregnated zeolite catalysts, at atmospheric pressure (total pressure), at a temperature of from 350 to 450° C., with a residence time of 40 seconds. Table 2 summarizes the distribution of metathesis products. Catalysts are denoted by metal ion (e.g., Ba, Co, Mn, etc.) and by type of Zeolyst Int'l. zeolite (e.g., 5524, 58, 8014, etc.). The mass (mg) of each product, as well as the total mass of products is given for each run. The abbreviations, B, PhBr, T, X, and M refer to benzene, phenyl bromide, toluene, xylene, and mesitylene, respectively.

TABLE 2

Metathesis of Brominated Methane Over Selected Catalysts.

| T (C.) | Catalyst | B | PhBr | T | X | M | Total (mg) |
|---|---|---|---|---|---|---|---|
| 350 | Ba 5524 | 0.25 | 0.00 | 0.96 | 2.58 | 3.14 | 6.93 |
| 350 | Ba 58 | 0.31 | 0.00 | 1.48 | 3.20 | 3.11 | 8.11 |
| 350 | Ba 8014 | 0.30 | 0.00 | 1.30 | 2.87 | 3.15 | 7.60 |
| 350 | Ca 58 | 0.20 | 0.00 | 0.81 | 2.44 | 3.09 | 6.53 |
| 350 | Co 2314 | 1.22 | 0.02 | 3.05 | 2.18 | 0.56 | 7.04 |
| 350 | Co 3024 | 0.36 | 0.00 | 2.06 | 4.21 | 3.47 | 10.10 |
| 350 | Co 58 | 0.20 | 0.00 | 1.05 | 2.91 | 3.34 | 7.50 |
| 350 | Mg 3024 | 0.31 | 0.00 | 1.53 | 3.59 | 3.89 | 9.32 |
| 350 | Mg 58 | 0.28 | 0.00 | 1.41 | 3.30 | 3.43 | 8.42 |
| 350 | Mn 2314 | 1.07 | 0.03 | 2.86 | 2.26 | 0.65 | 6.86 |
| 350 | Mn 3024 | 0.53 | 0.00 | 2.92 | 4.80 | 3.02 | 11.27 |
| 350 | Mn 58 | 0.17 | 0.00 | 0.88 | 2.70 | 3.62 | 7.37 |
| 350 | Ni 2314 | 1.12 | 0.05 | 2.94 | 2.44 | 0.74 | 7.29 |
| 350 | Ni 3024 | 0.61 | 0.00 | 2.82 | 3.85 | 2.13 | 9.41 |
| 375 | Ba 5524 | 0.32 | 0.00 | 1.32 | 2.82 | 2.57 | 7.04 |
| 375 | Ba 58 | 0.40 | 0.00 | 1.84 | 2.93 | 2.40 | 7.57 |
| 375 | Ba 8014 | 0.32 | 0.00 | 1.23 | 2.84 | 2.95 | 7.34 |
| 375 | Ca 58 | 0.20 | 0.00 | 0.96 | 2.55 | 2.93 | 6.64 |
| 375 | Co 3024 | 0.47 | 0.00 | 2.30 | 3.52 | 2.18 | 8.48 |
| 375 | Co 58 | 0.30 | 0.00 | 1.54 | 2.83 | 2.42 | 7.10 |
| 375 | Mg 3024 | 0.37 | 0.00 | 1.81 | 3.26 | 2.78 | 8.22 |
| 375 | Mg 58 | 0.34 | 0.00 | 1.67 | 3.04 | 2.74 | 7.80 |
| 375 | Mn 3024 | 0.62 | 0.00 | 2.91 | 3.90 | 2.17 | 9.59 |
| 375 | Mn 58 | 0.22 | 0.00 | 1.18 | 2.71 | 2.83 | 6.94 |
| 375 | Pd 2314 | 1.54 | 0.00 | 3.10 | 1.83 | 0.37 | 6.85 |
| 400 | Ba 5524 | 0.46 | 0.00 | 2.37 | 4.16 | 2.95 | 9.94 |
| 400 | Ba 58 | 0.70 | 0.00 | 3.15 | 3.91 | 2.70 | 10.47 |
| 400 | Ba 8014 | 0.38 | 0.00 | 1.57 | 3.81 | 3.77 | 9.53 |
| 400 | Ca 58 | 0.41 | 0.00 | 1.89 | 3.43 | 2.81 | 8.54 |
| 400 | Co 3024 | 0.78 | 0.00 | 3.42 | 4.14 | 2.26 | 10.60 |
| 400 | Co 58 | 0.62 | 0.00 | 2.71 | 3.36 | 2.31 | 8.99 |
| 400 | Mg 3024 | 0.76 | 0.00 | 3.26 | 4.11 | 2.64 | 10.76 |
| 400 | Mg 58 | 0.71 | 0.00 | 3.04 | 3.74 | 2.59 | 10.08 |
| 400 | Mn 3024 | 0.98 | 0.00 | 4.10 | 4.38 | 2.06 | 11.52 |
| 400 | Mn 58 | 0.48 | 0.00 | 2.26 | 3.44 | 2.64 | 8.82 |
| 400 | Ni 3024 | 0.81 | 0.00 | 3.15 | 3.35 | 1.72 | 9.04 |
| 400 | Pb 2314 | 1.20 | 0.03 | 3.25 | 3.27 | 1.20 | 8.94 |
| 400 | Pb 3024 | 1.07 | 0.04 | 2.77 | 3.63 | 1.66 | 9.17 |
| 400 | Pd 2314 | 2.44 | 0.00 | 3.16 | 1.22 | 0.18 | 7.01 |
| 400 | Sr 2314 | 2.13 | 0.01 | 4.05 | 2.29 | 0.46 | 8.94 |
| 400 | Sr 3024 | 1.93 | 0.05 | 4.03 | 2.67 | 0.65 | 9.32 |
| 425 | Ag 3024 | 2.79 | 0.02 | 4.16 | 1.78 | 0.29 | 9.04 |
| 425 | Ag 8014 | 3.09 | 0.02 | 3.52 | 1.09 | 0.16 | 7.88 |
| 425 | Ba 5524 | 0.54 | 0.00 | 2.67 | 3.67 | 2.33 | 9.22 |
| 425 | Ba 58 | 0.79 | 0.00 | 3.00 | 2.94 | 1.75 | 8.48 |
| 425 | Bi 2314 | 3.13 | 0.03 | 4.47 | 1.61 | 0.23 | 9.48 |
| 425 | Co 2314 | 3.39 | 0.03 | 4.34 | 1.59 | 0.25 | 9.60 |
| 425 | Co 3024 | 1.07 | 0.00 | 3.42 | 2.79 | 1.09 | 8.38 |
| 425 | Cu 2314 | 2.89 | 0.02 | 4.74 | 2.13 | 0.37 | 10.15 |
| 425 | Li 5524 | 1.51 | 0.04 | 3.31 | 3.27 | 1.12 | 9.24 |
| 425 | Mg 3024 | 0.99 | 0.00 | 3.28 | 2.85 | 1.37 | 8.48 |
| 425 | Mg 58 | 0.81 | 0.00 | 2.62 | 2.16 | 1.11 | 6.70 |
| 425 | Mn 3024 | 1.22 | 0.00 | 3.90 | 3.01 | 1.14 | 9.27 |
| 425 | Mo 2314 | 3.06 | 0.04 | 4.02 | 1.46 | 0.24 | 8.82 |
| 425 | Ni 3024 | 0.97 | 0.00 | 3.38 | 2.85 | 1.32 | 8.51 |
| 425 | Sr 3024 | 2.53 | 0.02 | 4.36 | 2.22 | 0.43 | 9.56 |

TABLE 2-continued

Metathesis of Brominated Methane Over Selected Catalysts.

| T (C.) | Catalyst | B | PhBr | T | X | M | Total (mg) |
|---|---|---|---|---|---|---|---|
| 450 | Ag 3024 | 3.84 | 0.02 | 4.27 | 1.36 | 0.18 | 9.67 |
| 450 | Bi 2314 | 3.90 | 0.01 | 3.59 | 0.67 | 0.06 | 8.23 |
| 450 | Ca 2314 | 3.64 | 0.02 | 4.10 | 1.00 | 0.16 | 8.92 |
| 450 | Co 2314 | 4.12 | 0.01 | 3.77 | 0.77 | 0.08 | 8.75 |
| 450 | Cu 2314 | 3.65 | 0.00 | 4.30 | 1.10 | 0.14 | 9.19 |
| 450 | Fe 2314 | 4.42 | 0.02 | 3.43 | 0.74 | 0.09 | 8.69 |
| 450 | Fe 3024 | 3.61 | 0.01 | 2.96 | 0.63 | 0.08 | 7.28 |
| 450 | Fe 5524 | 3.99 | 0.03 | 3.63 | 0.85 | 0.11 | 8.60 |
| 450 | La 2314 | 3.48 | 0.01 | 3.81 | 0.87 | 0.12 | 8.29 |
| 450 | Li 8014 | 1.74 | 0.02 | 2.61 | 2.67 | 0.84 | 7.89 |
| 450 | Mg 2314 | 4.20 | 0.02 | 3.84 | 0.76 | 0.10 | 8.92 |
| 450 | Mn 2314 | 3.78 | 0.02 | 3.90 | 0.88 | 0.12 | 8.70 |
| 450 | Mo 2314 | 3.88 | 0.01 | 3.26 | 0.58 | 0.06 | 7.79 |
| 450 | Ni 2314 | 4.39 | 0.01 | 3.12 | 0.44 | 0.03 | 8.00 |
| 450 | Pb 2314 | 2.58 | 0.01 | 4.68 | 2.31 | 0.45 | 10.02 |
| 450 | Pb 3024 | 2.08 | 0.01 | 4.44 | 2.87 | 0.70 | 10.10 |
| 450 | Pb 5524 | 1.89 | 0.02 | 3.58 | 2.71 | 0.73 | 8.93 |
| 450 | Pd 2314 | 4.03 | 0.00 | 1.58 | 0.14 | 0.00 | 5.76 |
| 450 | Sr 2314 | 3.71 | 0.00 | 4.78 | 1.68 | 0.21 | 10.39 |
| 450 | Sr 3024 | 2.51 | 0.01 | 3.76 | 1.61 | 0.26 | 8.14 |

EXAMPLE 5

Hydrodehalogenation of Bromobenzene, and Catalyst Regeneration

A test solution (1.5 ml/hr), which includes 1.9 wt % bromobenzene (PhBr) dissolved in dodecane, diluted by $N_2$ (1.1 ml/min) was fed into a tubular quartz reactor in which 3.6 g of highly dispersed precious metal catalyst ($Pd/Al_2O_3$, 0.5 wt %) was loaded. The reaction was carried out at 325° C. with a residence time of 15 s. The reaction effluent was trapped in a bubbler with 8 ml 4M NaOH solution pre-added. The carrier gas as well as the gaseous product were collected in a gas bag. All of the carbon-based products in the gas phase and oil phase in the liquid product were subjected to GC analysis. For the base trap solution, the HBr concentration was measured with an ion-selective electrode. Based on all of these measurements, carbon and bromine balances were calculated.

Figure 8:
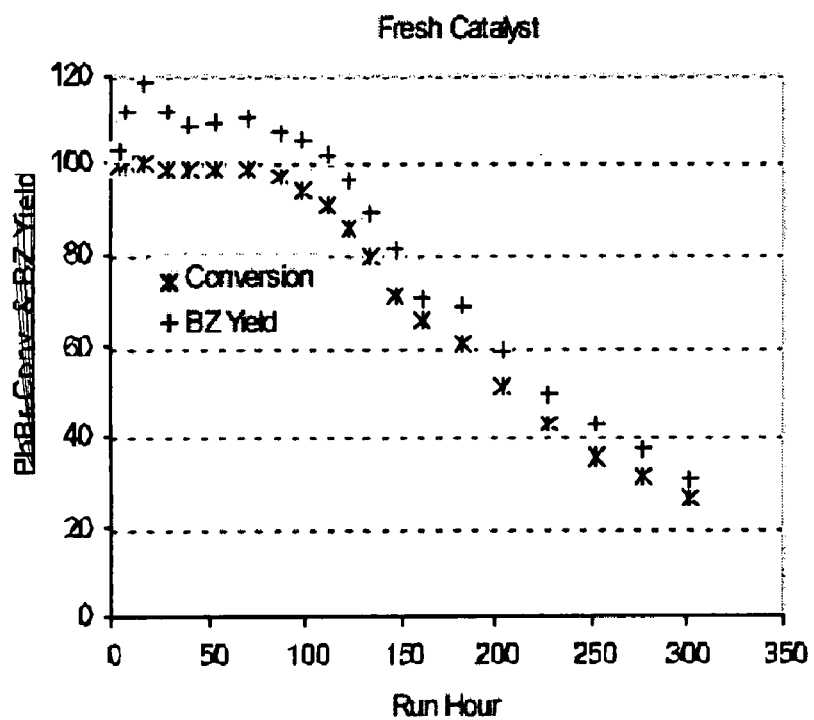
FIG. 8 is a graph of bromobenzene conversion and benzene yield as a function of time, for an experiment conducted according to one embodiment of the invention.
Figure 9:
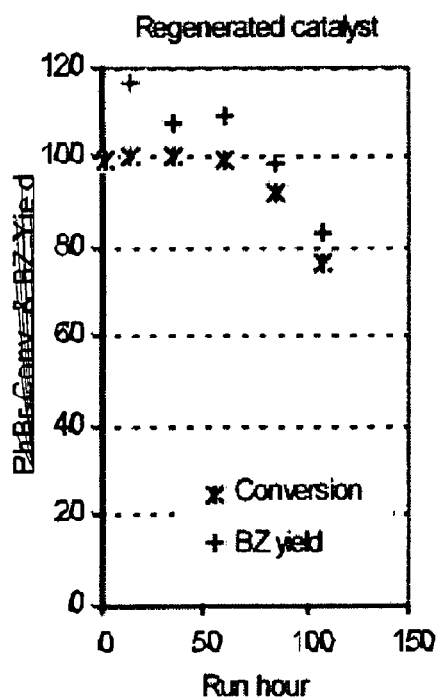
FIG. 9 is a graph of catalyst effectiveness as a function of time, for an experiment conducted according to one embodiment of the invention.

The experiment was continuously run for over 300 hours until the conversion of PhBr dropped from 100% in the initial 70 hrs to below 30% (FIG. 8). Hydrodebromination of PhBr took place over the catalyst bed with the formation of benzene ("BZ") and HBr as the major products, accompanied with some light hydrocarbons ($C_3$-$C_7$) being detected as byproducts, which originated from solvent decomposition. Carbon deposition was recognized as the primary reason for deactivation of the catalyst. The catalyst proved to be re-generable via decoking at 500° C. with $O_2$ oxidation (5 ml/min) for 10 hrs, followed by $H_2$ reduction (20 ml/min) at 400° C. for 3 hrs. The regenerated catalyst was identified to be as effective as the fresh catalyst, as confirmed by its ability to catalyze the same hydrodebromination reaction without activity loss in the first 70 hours (FIG. 9).

The invention has been described with references to various examples and preferred embodiments, but is not limited thereto. Other modifications and equivalent arrangements, apparent to a skilled person upon consideration of this disclosure, are also included within the scope of the invention. For example, in an alternate embodiment of the invention, the products 25 from the bromine generation reactor are fed directly into the bromination reactor 3. The advantage of such a configuration is in eliminating the bromine holdup needed in the flash unit 27, thereby reducing the handling of liquid bromine. Also, by eliminating the bromine scavenging section including units 26, 27, 31 and 34, the capital cost for the process can be reduced significantly. For energy efficiency, it is desirable to have the outlet of bromine generation be equal to the bromination temperature. For bromine generation, cerium-based catalysts are therefore preferred over copper-based catalysts in this embodiment, since cerium bromide has a higher melting point (722° C.) than copper (I) bromide (504° C.). The presence of oxygen in bromination and coupling reduces the selectivity to the desired products; therefore, the bromine generation reactor must consume all of the oxygen in the feed. In this embodiment, the monobromide separation 5 must be modified to remove water using a liquid-liquid split on the bottoms stream of the distillation column 51. The water removed in the liquid-liquid split contains HBr, which can be removed from water using extractive distillation (see, e.g., FIG. 5), and then recycled back to the bromine generation section.

Still other modifications are within the scope of the invention, which is limited only by the accompanying claims and their equivalents.

What is claimed is:

1. A continuous process for converting a hydrocarbon feedstock into one or more higher hydrocarbons, comprising:
   (a) forming alkyl halides by reacting molecular halogen with a hydrocarbon feedstock containing methane, under process conditions sufficient to form alkyl halides and hydrogen halide, whereby substantially all of the molecular halogen is consumed;
   (b) forming reproportionated alkyl halides by reacting some or all of the alkyl halides with an alkane feed, whereby the fraction of monohalogenated hydrocarbons present is increased;
   (c) contacting the reproportionated alkyl halides with a first catalyst under process conditions sufficient to form higher hydrocarbons and additional hydrogen halide;
   (d) separating the higher hydrocarbons from the hydrogen halide;
   (e) regenerating molecular halogen by contacting the hydrogen halide with a second catalyst in the presence of a source of oxygen, under process conditions sufficient to form molecular halogen and water;
   (f) separating the molecular halogen from water to allow reuse of the halogen; and
   (g) repeating steps (a) through (f) a desired number of times.

2. A continuous process as recited in claim 1, further comprising separating monohalogenated alkyl halides from polyhalogenated alkyl halides after steps (a) and/or (b).

3. A continuous process as recited in claim 1, wherein the hydrocarbon feedstock comprises one or more $C_1$-$C_4$ hydrocarbons.

4. A continuous process as recited in claim 1, wherein the hydrocarbon feedstock comprises natural gas.

5. A continuous process as recited in claim 1, wherein the halogen comprises bromine.

6. A continuous process as recited in claim 1, wherein the halogen comprises chlorine.

7. A continuous process as recited in claim 1, wherein the alkane feed contains at least 1% by volume of one or more C2-C5 hydrocarbons.

8. A continuous process as recited in claim 1, wherein the amount of monohalogenated alkyl halide(s) present is increased in the presence of a reproportionation catalyst.

9. A continuous process as recited in claim 1, wherein the reproportionation catalyst comprises a metal, metal-oxygen material, or metal halide.

10. A continuous process as recited in claim 1, wherein the first catalyst comprises a zeolite.

11. A continuous process as recited in claim 10, wherein the zeolite comprises a metal-doped or ion-exchanged zeolite.

12. A continuous process as recited in claim 10, wherein the zeolite is doped with manganese.

13. A continuous process as recited in claim 1, wherein the second catalyst comprises at least one material selected from the group consisting of CaO, $CeO_2$, $Co_3O_4$, CuO, NiO, MgO, carbides, nitrides, carbons, and clays.

14. A continuous process as recited in claim 1, wherein the second catalyst comprises CuO or $CeO_2$.

15. A continuous process as recited in claim 1, wherein the second catalyst comprises at least one material selected from the group consisting of halides, oxides, and oxyhalides of Ag, Au, Ba, Ca, Ce, Co, Cr, Cu, Fe, Mg, Mn, Mo, Nb, Ni, Pb, Pd, Pt, Sr, Ta, V, W, Mg, V, or Zn.

16. A continuous process as recited in claim 1, wherein the hydrogen halide separated from the higher hydrocarbons comprises HBr and aqueous hydrobromic acid, and wherein HBr is separated from aqueous hydrobromic acid using pressure swing distillation or extractive distillation.

17. A continuous process as recited in claim 16, wherein separation of the HBr from the aqueous hydrobromic acid comprises utilizing extractive distillation with an aqueous solution of $CaBr_2$, $MgBr_2$, KBr, NaBr, LiBr or mixtures thereof used as an extracting agent.

18. A continuous process as recited in claim 16, wherein separation of the HBr from the aqueous hydrobromic acid comprises utilizing extractive distillation with sulfuric acid used as an extracting agent.

19. A continuous process as recited in claim 1, wherein the alkane feed used for reproportionation comprises a hydrocarbon feed gas containing significant quantities of C2-C5 hydrocarbons.

20. A continuous process as recited in claim 1, wherein the formation of alkyl halides and the formation of reproportionated alkyl halides are carried out in separate reactors.

21. A continuous process for converting a hydrocarbon feedstock into one or more higher hydrocarbons, comprising:

(a) forming alkyl halides by reacting molecular halogen with a hydrocarbon feedstock containing methane in a halogenation reactor, under process conditions sufficient to form alkyl halides and hydrogen halide, whereby substantially all of the molecular halogen is consumed;

(b) separating unreacted methane from the alkyl halides and directing it back into the halogenation reactor;

(c) forming reproportionated alkyl halides by reacting some or all of the alkyl halides with an alkane feed containing at least 1% by volume of C2-C5 hydrocarbons, whereby the fraction of monohalogenated hydrocarbons present is increased;

(d) contacting the reproportionated alkyl halides with a first catalyst under process conditions sufficient to form higher hydrocarbons and additional hydrogen halide;

(e) separating the higher hydrocarbons from the hydrogen halide;

(f) regenerating molecular halogen by contacting the hydrogen halide with a second catalyst in the presence of a source of oxygen, under process conditions sufficient to form molecular halogen and water;

(g) separating the molecular halogen from water to allow reuse of the halogen; and (h) repeating steps (a) through (g) a desired number of times.

22. A continuous process as recited in claim 21, wherein formation of alkyl halides and formation of reproportionated alkyl halides are carried out in separate reactors.

* * * * *

UNITED STATES PATENT AND TRADEMARK OFFICE
CERTIFICATE OF CORRECTION

PATENT NO. : 7,579,510 B2
APPLICATION NO. : 11/703358
DATED : August 25, 2009
INVENTOR(S) : Sagar B. Gadewar et al.

It is certified that error appears in the above-identified patent and that said Letters Patent is hereby corrected as shown below:

Claim 9, column 23, line 1
After "as recited in claim", insert --8-- and delete "1".

Signed and Sealed this
Twenty-second Day of February, 2011

David J. Kappos
*Director of the United States Patent and Trademark Office*